(12) United States Patent
Katahira

(10) Patent No.: US 8,449,127 B2
(45) Date of Patent: May 28, 2013

(54) ENDOSCOPE OBJECTIVE LENS AND ENDOSCOPE USING THE SAME

(75) Inventor: Yuko Katahira, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/340,025

(22) Filed: Dec. 29, 2011

(65) Prior Publication Data

US 2012/0154932 A1 Jun. 21, 2012

Related U.S. Application Data

(63) Continuation of application No. PCT/JP2010/072245, filed on Dec. 10, 2010.

(30) Foreign Application Priority Data

Dec. 24, 2009 (JP) ................................. 2009-292371

(51) Int. Cl.
*G02B 5/22* (2006.01)
*G02B 9/04* (2006.01)
*A61B 1/00* (2006.01)
*A61B 19/00* (2006.01)

(52) U.S. Cl.
USPC ............ 359/871; 359/795; 600/101; 128/898

(58) Field of Classification Search
USPC .. 359/738–740, 745–795, 871; 600/101–183; 128/898
See application file for complete search history.

(56) References Cited

U.S. PATENT DOCUMENTS

| 6,327,101 B1 | 12/2001 | Miyano |
| 2003/0040422 A1 | 2/2003 | Kikuchi et al. |

FOREIGN PATENT DOCUMENTS

| JP | 62-173415 | 7/1987 |
| JP | 06-230280 | 8/1994 |
| JP | 6-308381 | 11/1994 |
| JP | 9-80305 | 3/1997 |
| JP | 11-052238 | 2/1999 |
| JP | 2000-330015 | 11/2000 |
| JP | 2004-012504 | 1/2004 |
| JP | 2004-029282 | 1/2004 |
| JP | 3 574 484 | 7/2004 |
| JP | 2004-354888 | 12/2004 |
| JP | 2006-251272 | 9/2006 |
| JP | 2007-249189 | 9/2007 |
| JP | 2008-83316 | 4/2008 |
| JP | 2008-224842 | 9/2008 |
| JP | 4 229 754 | 12/2008 |
| JP | 4 245 985 | 1/2009 |
| JP | 2009-080413 | 4/2009 |
| JP | 2009-163256 | 7/2009 |

OTHER PUBLICATIONS

European Search Report, dated Oct. 8, 2012, issued in corresponding European Patent Application No. 10839206.9.

*Primary Examiner* — Dawayne A Pinkney
(74) *Attorney, Agent, or Firm* — Kenyon & Kenyon LLP

(57) ABSTRACT

An endoscope objective lens includes, in sequence from an object side, a front group which includes a negative first lens having a concave surface faces at image side, a filter, and a positive second lens having a convex surface at the object side and a flat surface or concave surface at the image side; an aperture stop; and a back group which includes a positive third lens having a convex surface at the image side, and a combined lens formed of a plano-convex lens or a biconvex lens and a negative meniscus lens, and satisfies the Conditional Expression (1) and (2):

$$n3 > -v3/12 + 5.5, \qquad (1)$$

$$2.0 > df/Ih > 1.5. \qquad (2)$$

3 Claims, 26 Drawing Sheets

ENDOSCOPE OBJECTIVE LENS AND ENDOSCOPE USING THE SAME

CROSS-REFERENCE TO RELATED APPLICATIONS

This is a continuation of International Application PCT/JP2010/072245, with an international filing date of Dec. 10, 2010, which is hereby incorporated by reference herein in its entirety. This application claims the benefit of Japanese Patent Application No. 2009-292371, the content of which is incorporated herein by reference.

BACKGROUND OF THE INVENTION

1. Field of the Invention

The present invention relates to an endoscope objective lens that has a simple configuration and is suitable for a compact, high-resolution image acquisition device usable in laser treatment and the like, and to an endoscope using the same.

2. Description of Related Art

In endoscopes used in the medical field etc., in order to improve the operability and reduce stress on patients, it has been necessary to reduce the diameter of endoscope insertion portions and to reduce the length of rigid portions at the tip. Therefore, objective lenses installed therein must be configured to have a small outside diameter and a small overall length. Compact endoscope objective lenses having a simple configuration are known (for example, see The Publication of Japanese Patent No. 4245985 and Japanese Unexamined Patent Application, Publication No. 2007-249189).

On the other hand, in the case of endoscopes usable in laser treatment and the like, a filter, such as a laser-light cut filter or a color-correcting filter, needs to be inserted into the objective lens. Endoscopes having such filters are known (for example, see the Publication of Japanese Patent No. 4245985, the Publication of Japanese Patent No. 4229754, the Publication of Japanese Patent No. 3574484 and Japanese Unexamined Patent Application, Publication No. 2004-354888). In the Publication of Japanese Patent No. 4245985, the Publication of Japanese Patent No. 4229754, and the Publication of Japanese Patent No. 3574484, a filter is disposed near the image plane, not at a position immediately behind the aperture stop where the angle of incidence on the filter is large. In Example 9 in Japanese Unexamined Patent Application, Publication No. 2004-354888, a filter is disposed in immediate proximity to the image plane. In Example 11 in Japanese Unexamined Patent Application, Publication No. 2004-354888, filters are disposed immediately in front of the aperture stop and between the aperture stop and a combined lens disposed therebehind.

Meanwhile, in order to improve the diagnostic capability using an endoscope, it is important to improve image quality by correcting various optical aberrations. Endoscope objective lenses achieve a wide angle of view by employing a retrofocus structure, in which a lens group having negative refractive power is disposed on the object side of the aperture stop, and a lens group having positive refractive power is disposed on the image side of the aperture stop. However, because this configuration is asymmetrical with respect to the aperture stop, correcting lateral chromatic aberration is especially difficult. Objective lenses in which such lateral chromatic aberration is effectively corrected are known (for example, see Japanese Unexamined Patent Application, Publication No. 2007-249189).

BRIEF SUMMARY OF THE INVENTION

A first aspect of the present invention is an endoscope objective lens comprising, in sequence from an object side, a front group, an aperture stop, and a back group, wherein the front group includes, in sequence from the object side, a negative first lens whose concave surface faces an image side and a positive second lens whose convex surface faces the object side and whose flat surface or concave surface is located on the image side, and a filter disposed between the first lens and second lens, and the back group includes, in sequence from the object side, a positive third lens whose convex surface faces the image side, and a combined lens formed of a plano-convex lens or a biconvex lens and a negative meniscus lens, and the endoscope objective lens satisfies the following Conditional Expression (1) and (2)

$$n3 > -v3/12 + 5.5 \quad (1)$$

$$2.0 > df/Ih > 1.5 \quad (2)$$

where $n3$ is the refractive index of the third lens, and $v3$ is the Abbe number of the third lens, $df$ is the sum of the thickness of an optical element and the inter-surface distance from the apex of the concave surface of the first lens to the aperture stop, and $Ih$ is the maximum image height.

A second aspect of the present invention is an endoscope including the above-described endoscope objective lenses.

DETAILED DESCRIPTION OF THE INVENTION

Figure 1:
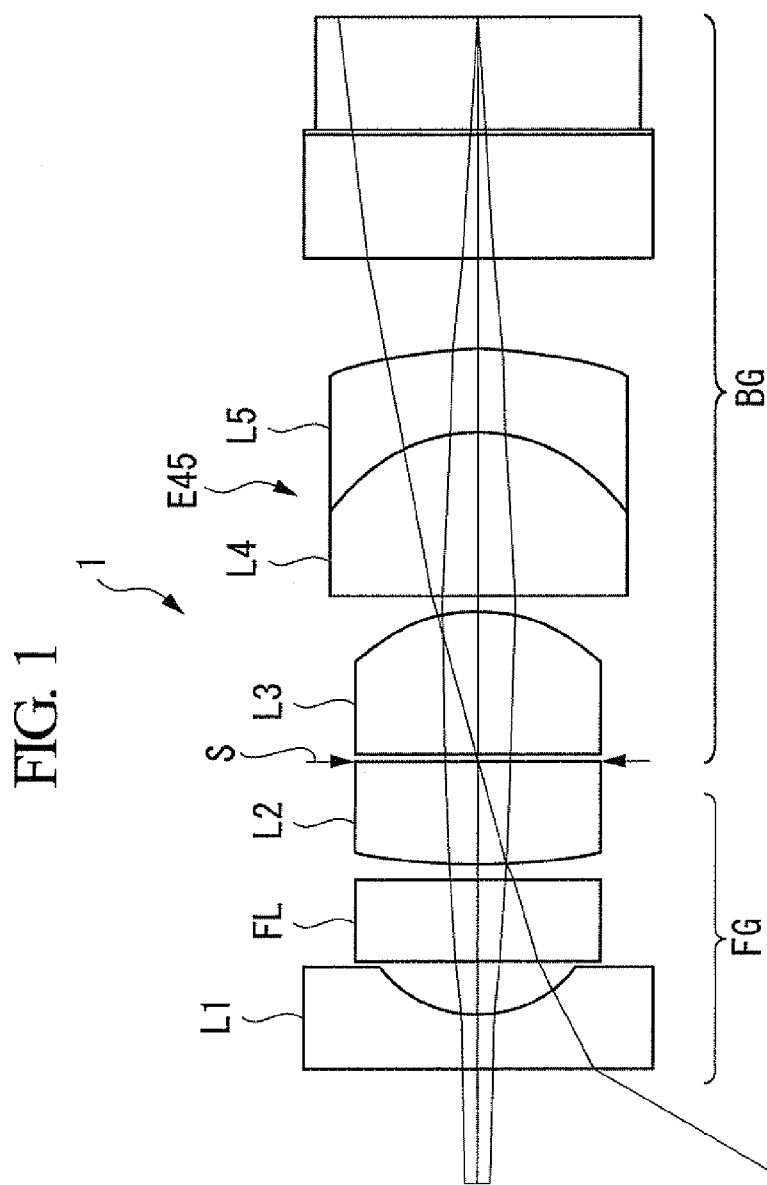
FIG. 1 is a lens cross-sectional diagram showing the configuration of an endoscope objective lens according to an embodiment of the present invention.

Referring to FIG. 1, an endoscope objective lens 1 according to an embodiment of the present invention will be described below.

As shown in FIG. 1, the endoscope objective lens 1 according to this embodiment is formed of, in sequence from the object side, a front group FG, an aperture stop S, and a back group BG.

The front group FG includes, in sequence from the object side, a negative first lens L1 whose concave surface faces the image side, a positive second lens L2 whose convex surface faces the object side and whose flat surface is located on the image side, and a filter FL disposed between the first lens L1 and the second lens L2. Any filter, such as a laser-light cut filter, a color-correcting filter, a transmission filter, an absorption filter, a reflection filter, or a polarizing filter, may be appropriately used as the filter FL.

Sapphire is preferably used as the glass material of the first lens L1. Sapphire is advantageous in correcting lateral chromatic aberration because it has a high Abbe number (vd=71.79) and is also advantageous in correcting coma because it has a high refractive index (nd=1.7682). In addition, sapphire is preferable for the first lens L1, which is externally exposed, because it is tolerant of high-temperature, high-pressure steam sterilization, called autoclave sterilization, and of chemicals used in chemical cleaning, which is usually performed in the use of endoscopes. A glass material having high sterilization resistance and chemical resistance, such as zirconia, Yttria-stabilized zirconia, synthetic quartz, transparent YAG, or spinel, may be used instead of sapphire.

The back group BG includes, in sequence from the object side, a positive third lens L3 whose convex surface faces the image side, and a combined lens E45 formed of a plano-convex lens or a biconvex lens (in the example shown, a plano-convex lens) L4 and a negative meniscus lens L5. The back group BG satisfies the following Conditional Expression (1)

$$n3 > -v3/12 + 5.5 \quad (1)$$

where n3 is the refractive index of the third lens L3, and v3 is the Abbe number of the third lens L3.

Conditional Expression (1) defines the refractive index and Abbe number of the positive third lens in the back group. To correct chromatic aberration, it is preferable that the positive lens in the back group be composed of a material having a large Abbe number. By disposing the positive lens having small dispersion immediately behind the aperture stop, the lateral chromatic aberration can be effectively corrected. If Conditional Expression (1) is not satisfied, it is difficult to correct chromatic aberration in the entire system.

The endoscope objective lens 1 also satisfies the following Conditional Expressions (2) and (3)

$$2.0 > df/Ih > 1.5 \quad (2)$$

$$|f3/r3| > 1.3 \quad (3)$$

where, df is the sum of the thicknesses of the optical element (the filter FL and the second lens L2) and the inter-surface distance from the apex of the concave surface of the first lens L1 to the aperture stop S, and Ih is the maximum image height, f3 is the focal length of the third lens L3, r3 is the image-plane-side radius of curvature of the third lens L3.

In order to dispose the filter in the front group, a sufficient space in view of the size of the image acquisition device needs to be ensured in the front group. Conditional Expression (2) defines the proportion of the sum of the thickness of an optical element and the inter-surface distance from the apex of the concave surface of the first lens to the aperture stop to the maximum image height. If the lower limit of Conditional Expression (2), namely, 1.5, is not reached, it is difficult to ensure a sufficient space for disposing the filter or the like. If the upper limit 2.0 of Conditional Expression (2) is exceeded, although a space for disposing the filter or the like can be ensured, a need to increase the distance between the position behind the aperture stop and the image plane arises. As a result, the angle of incidence on the image plane increases, which may cause a shading phenomenon.

Conditional Expression (3) defines the proportion of the focal length of the positive third lens in the back group to the radius of curvature of the image-side surface. In order to reduce the overall length and minimize variations in the angle of incidence on the image plane in a compact endoscope objective lens, light needs to be bent by a small number of lenses disposed on the rear side of the aperture stop. From the standpoint of the lens manufacturing and the assembly precision, it is desirable that the radius of curvature of the lens be larger than a certain value. Therefore, the focal length and the radius of curvature of the image-side surface of the third lens need to be balanced. If the lower limit of Conditional Expression (3), namely, 1.3, is not reached, although the angle of incidence on the image plane can be corrected so as to be parallel to the optical axis, because the radius of curvature of the image-side surface of the third lens increases, correcting chromatic aberration becomes difficult in the entire system, and lens processing conditions become severe.

The thus-configured endoscope objective lens 1 can reduce the risk of damaging the filter FL during assembly by disposing the optical filter FL, which is a laser-light cut filter or the like, between the lenses L1 and L2. Furthermore, by simultaneously satisfying Conditional Expressions (1) to (3), a compact configuration can be achieved while effectively correcting all optical aberrations, including lateral chromatic aberration, in a balanced manner. Therefore, the endoscope objective lens 1 can be suitably used in an endoscope having a compact, high-resolution image acquisition device usable in laser treatment and the like. Furthermore, by disposing the filter FL closer to the object side, the angle of incidence of light on the filter FL is reduced. Thus, color correction and blocking of light having wavelengths in the infrared region can be more effectively performed.

In the above-described embodiment, the back group BG may include a plurality of lenses having positive refractive power. For example, a sixth lens having a positive refractive index may be used as an optical component 3. This configuration is advantageous in correcting field curvature because the angle of incidence on the image plane can be corrected so as to be parallel to the optical axis by disposing a lens having positive refractive power near the image plane.

Furthermore, in the above-described embodiment, an optical-path changing device, such as a prism or the like, may be disposed somewhere in the optical path.

For example, a prism is disposed on the object side of the image acquisition device to change the optical path in a direction perpendicular to the optical axis. By doing so, even when a large image acquisition device is used, an image acquisition surface of the image acquisition device can be disposed parallel to the optical axis, and the diameter of the tip of the endoscope can be reduced. Note that the direction in which the optical path is changed is not limited to a direction perpendicular to the optical axis.

Furthermore, in the above-described embodiment, the filter FL may be disposed behind the second lens L2 in the front group FG. Also with this configuration, similarly to the above-described embodiment, damage to the filter FL can be prevented, and a reduction in size can be achieved while effectively correcting various aberrations.

EXAMPLES

Next, examples of the above-described embodiment will be described below with reference to FIGS. 2 to 26. In the lens cross-sectional diagrams, r represents the radius of curvature, d represents the inter-surface distance, and the number following r or d represents the surface number. In the respective aberration diagrams, (a) represents spherical aberration, (b) represents astigmatism, (c) represents lateral chromatic aberration, (d) represents coma in the M direction, and (e) represents coma in the S direction. Furthermore, the aberration diagrams show aberrations for the d line (587.56 nm), serving as the reference wavelength, and aberrations for the C line (656.27 nm), the F line (486.13 nm), and the g line (435.83 nm) are also shown in the diagrams showing spherical aberration, lateral chromatic aberration, and coma. Furthermore, for coma, coma in a ray direction (M direction) and coma in a concentric circle direction (S direction) are shown. The refractive indices listed in the lens data are the refractive indices for the d line. In the lens data shown in each example, r is radius of curvature, d is inter-surface distance, nd is refractive index, ν is Abbe number, OBJ is object plane, IMG is image plane and S is stop.

Example 1

Figure 2:
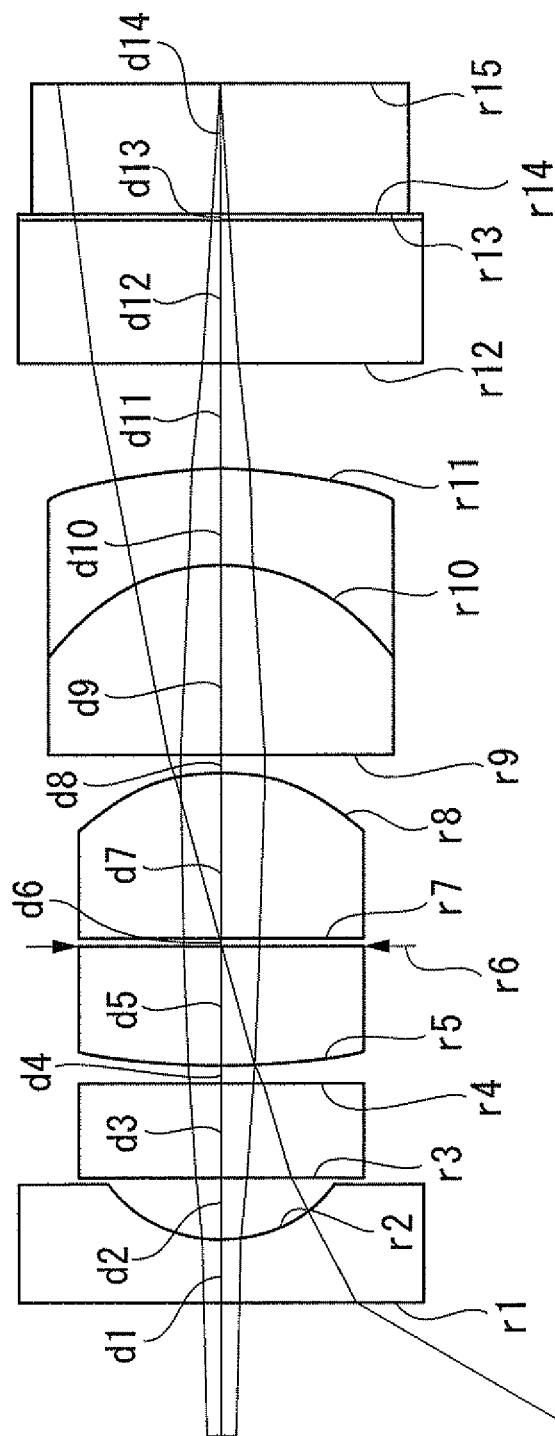
FIG. 2 is a lens cross-sectional diagram showing the configuration of an endoscope objective lens according to Example 1.
Figure 3:
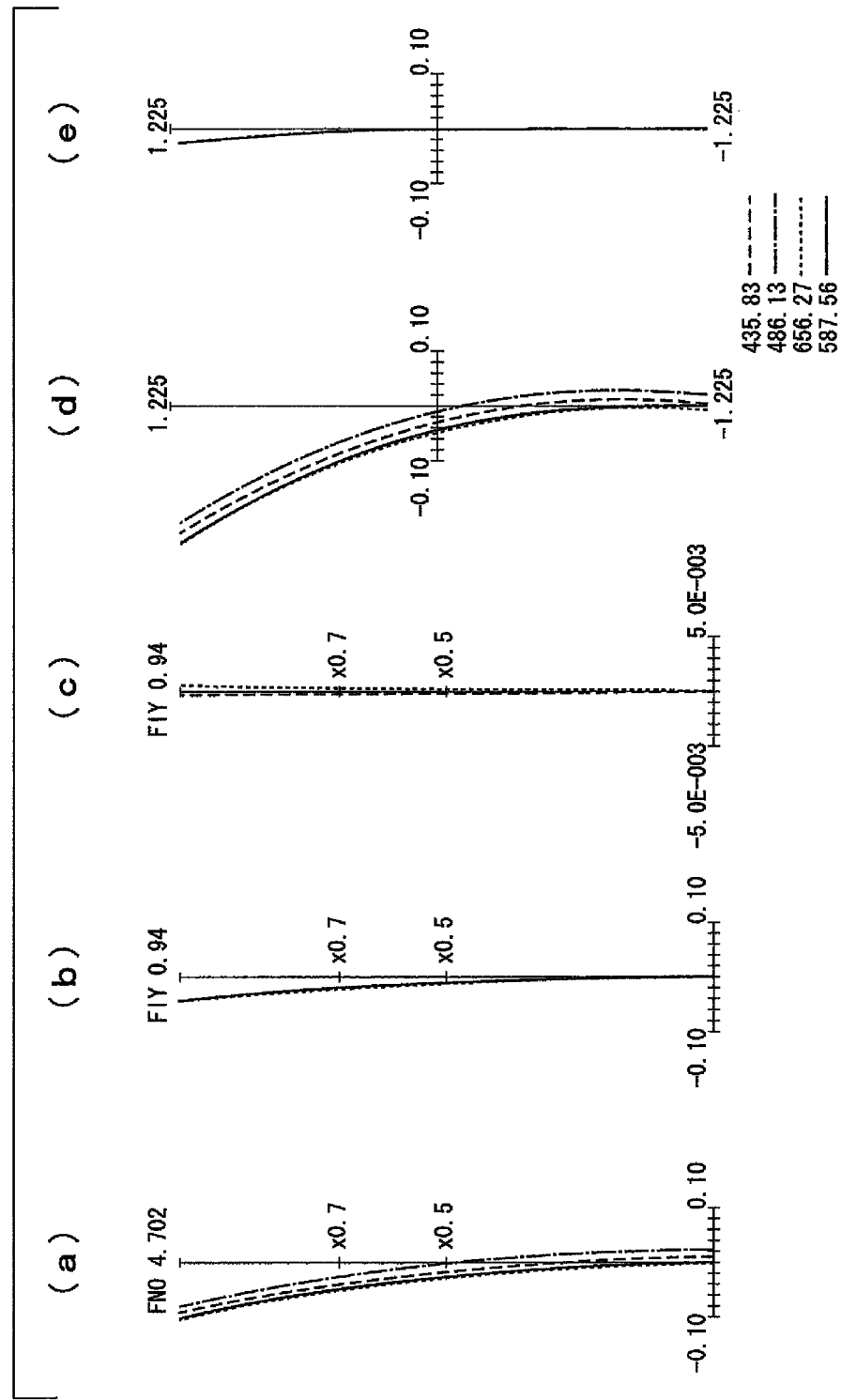
FIG. 3 includes various kinds of aberration diagrams of the endoscope objective lens in FIG. 2.

FIG. 2 shows the configuration of an endoscope objective lens according to Example 1, and the lens data thereof are shown below. FIG. 3 shows aberration diagrams of the objective lens according to this example.

The endoscope objective lens according to this example is formed of, in sequence from the object side, a front group, an aperture stop, and a back group. The front group is formed of, in sequence from the object side, a negative first lens whose concave surface faces the image side, a filter, and a positive second lens whose convex surface faces the object side and whose flat surface is located on the image side. The back group is formed of, in sequence from the object side, a positive third lens whose convex surface faces the image side, and a combined lens formed of a plano-convex lens and a negative meniscus lens.

| Lens Data | | | | |
|---|---|---|---|---|
| Surface Number | r | d | nd | ν |
| OBJ | ∞ | 10.3427 | 1.000 | |
| 1 | ∞ | 0.3629 | 1.768 | 71.79 |
| 2 | 0.8535 | 0.3386 | 1.000 | |
| 3 | ∞ | 0.5444 | 1.518 | 75.00 |
| 4 | ∞ | 0.1089 | 1.000 | |
| 5 | 3.8738 | 0.6858 | 1.750 | 35.33 |
| 6(S) | ∞ | 0.0544 | 1.000 | |
| 7 | ∞ | 0.9389 | 1.700 | 65.00 |
| 8 | −1.1501 | 0.0907 | 1.000 | |
| 9 | ∞ | 1.0901 | 1.729 | 54.68 |
| 10 | −1.2076 | 0.5444 | 1.923 | 18.90 |
| 11 | −3.1972 | 0.6169 | 1.000 | |
| 12 | ∞ | 0.8165 | 1.516 | 64.14 |
| 13 | ∞ | 0.0363 | 1.510 | 64.05 |
| 14 | ∞ | 0.7258 | 1.611 | 50.49 |
| 15 | ∞ | 0.0000 | 1.000 | |
| IMG | ∞ | 0.0000 | | |

Example 2

Figure 4:
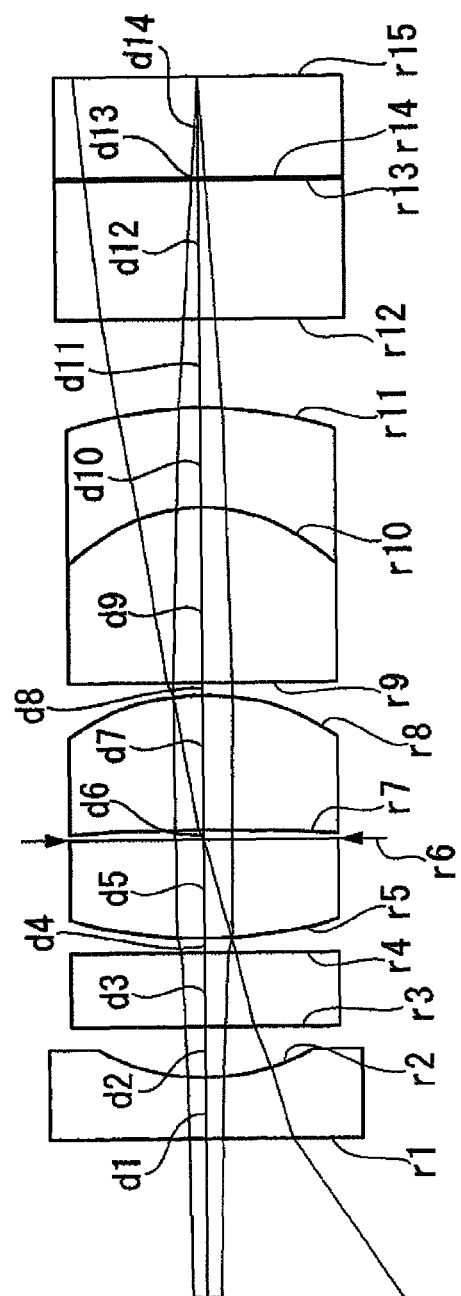
FIG. 4 is a lens cross-sectional diagram showing the configuration of an endoscope objective lens according to Example 2.
Figure 5:
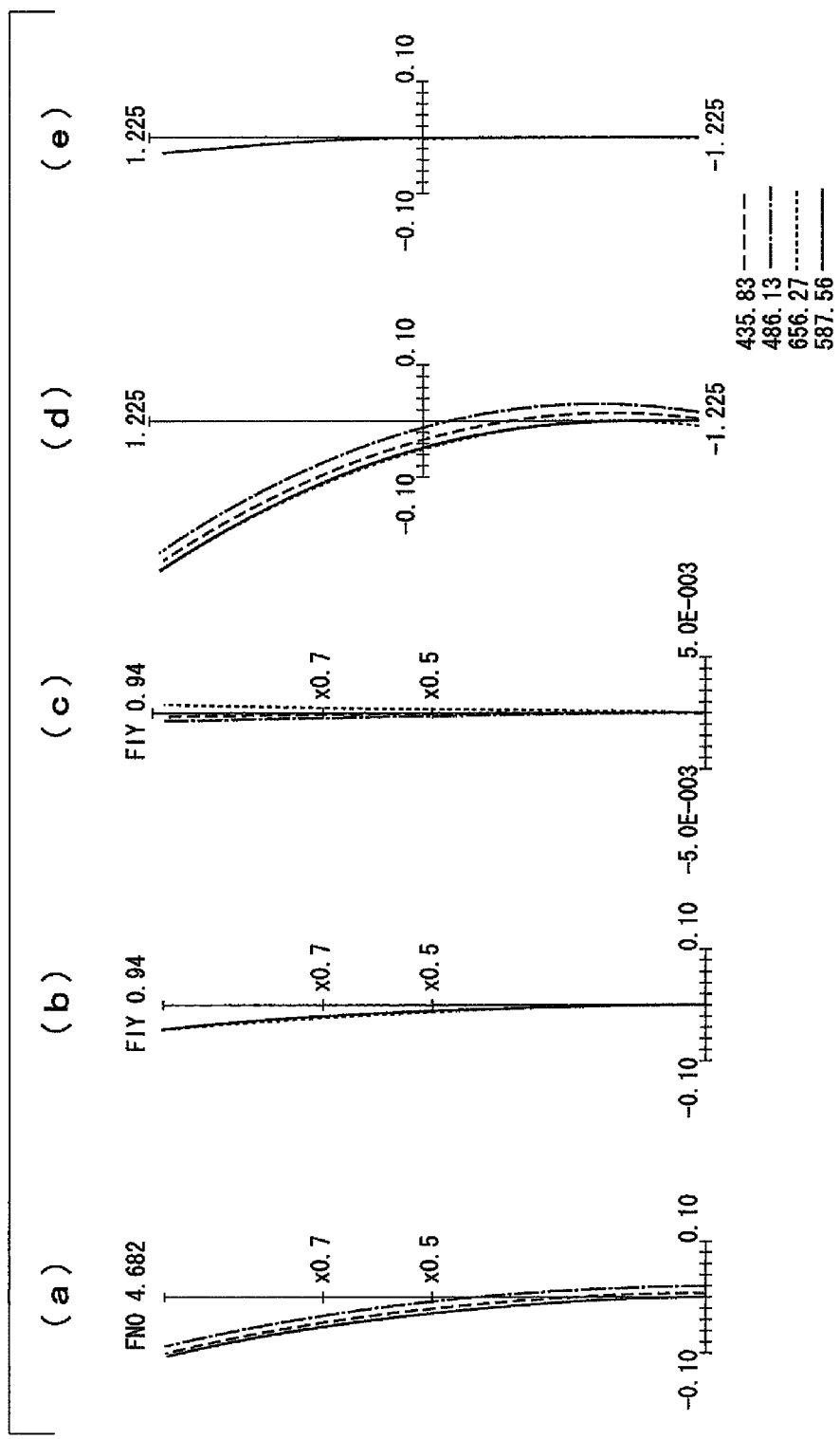
FIG. 5 includes various kinds of aberration diagrams of the endoscope objective lens in FIG. 4.

FIG. 4 shows the configuration of an endoscope objective lens according to Example 2, and the lens data thereof are shown below. FIG. 5 shows aberration diagrams of the endoscope objective lens according to this example.

The endoscope objective lens according to this example has the same configuration as the endoscope objective lens according to Example 1.

| Lens Data | | | | |
|---|---|---|---|---|
| Surface Number | r | d | nd | ν |
| OBJ | ∞ | 10.3437 | 1.0000 | |
| 1 | ∞ | 0.3629 | 1.7710 | 71.79 |
| 2 | 0.8688 | 0.3462 | 1.0000 | |
| 3 | ∞ | 0.5444 | 1.5200 | 75.00 |
| 4 | ∞ | 0.1089 | 1.0000 | |
| 5 | 4.0328 | 0.6824 | 1.7550 | 35.33 |
| 6(S) | ∞ | 0.0544 | 1.0000 | |
| 7 | ∞ | 0.9529 | 1.6830 | 62.00 |
| 8 | −1.1187 | 0.0907 | 1.0000 | |
| 9 | ∞ | 1.0893 | 1.7320 | 54.68 |
| 10 | −1.2089 | 0.5444 | 1.9340 | 18.90 |
| 11 | −3.1975 | 0.6170 | 1.0000 | |
| 12 | ∞ | 0.8166 | 1.5180 | 64.14 |
| 13 | ∞ | 0.0363 | 1.5120 | 64.05 |
| 14 | ∞ | 0.7259 | 1.6140 | 50.49 |
| 15 | ∞ | 0.0000 | 1.0000 | |
| IMG | ∞ | 0.0000 | | |

Example 3

Figure 6:
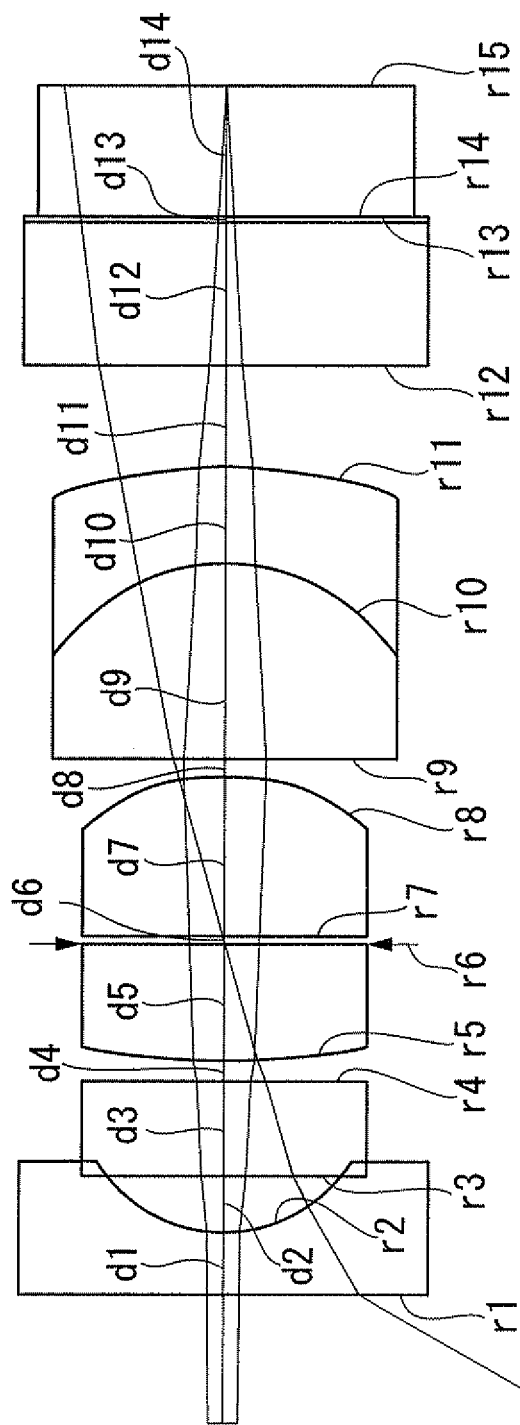
FIG. 6 is a lens cross-sectional diagram showing the configuration of an endoscope objective lens according to Example 3.
Figure 7:
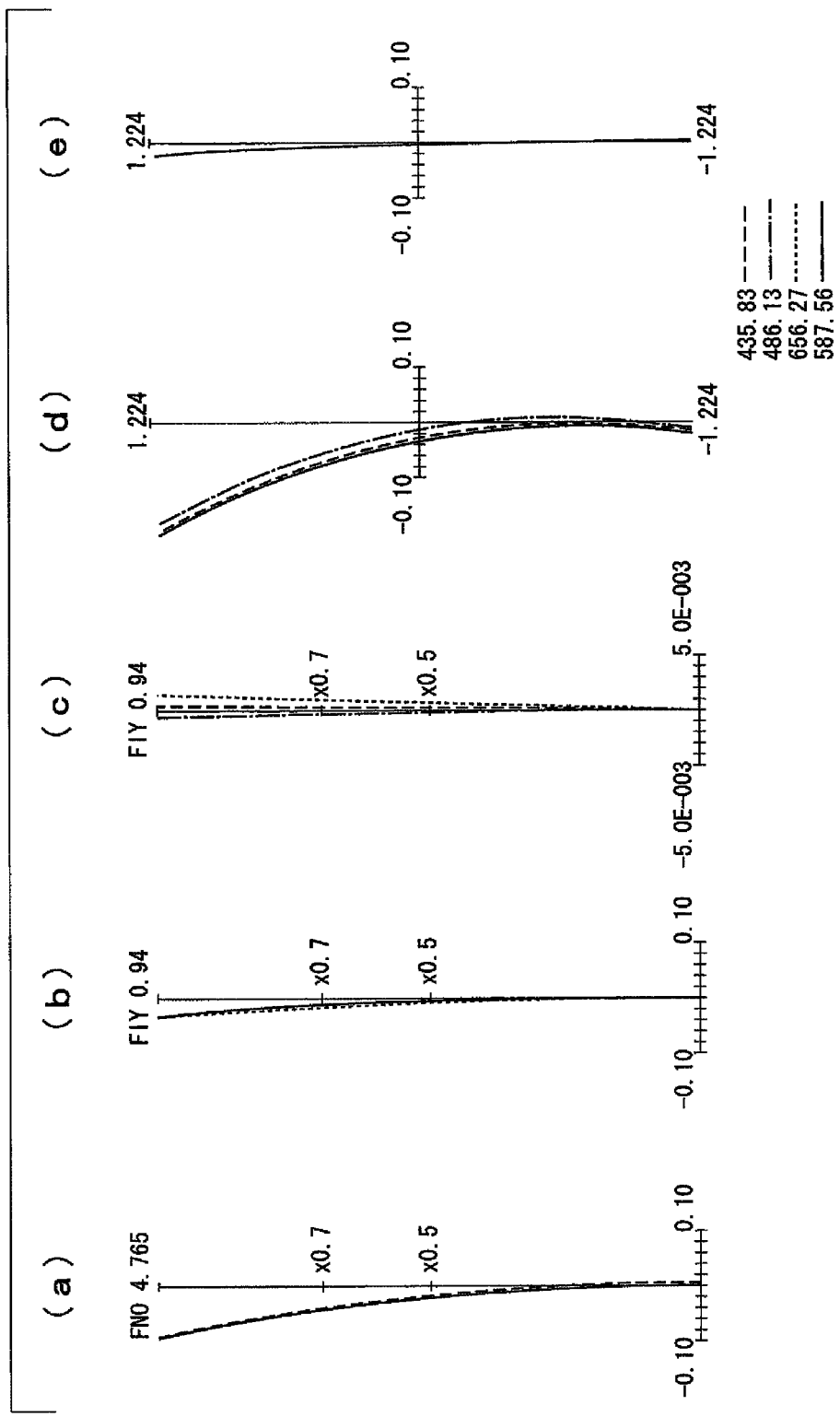
FIG. 7 includes various kinds of aberration diagrams of the endoscope objective lens in FIG. 6.

FIG. 6 shows the configuration of an endoscope objective lens according to Example 3, and the lens data thereof are shown below. FIG. 7 shows aberration diagrams of the endoscope objective lens according to this example.

The endoscope objective lens according to this example has the same configuration as the endoscope objective lens according to Example 1.

| Lens Data | | | | |
|---|---|---|---|---|
| Surface Number | r | d | nd | ν |
| OBJ | ∞ | 10.3362 | 1.0000 | |
| 1 | ∞ | 0.3627 | 1.7710 | 71.79 |
| 2 | 0.8436 | 0.3445 | 1.0000 | |
| 3 | ∞ | 0.5440 | 1.5200 | 75.00 |
| 4 | ∞ | 0.1088 | 1.0000 | |
| 5 | 4.2176 | 0.6781 | 1.7550 | 35.33 |
| 6(S) | ∞ | 0.0544 | 1.0000 | |
| 7 | ∞ | 0.9213 | 1.7440 | 48.00 |
| 8 | −1.1926 | 0.0907 | 1.0000 | |
| 9 | ∞ | 1.1388 | 1.7320 | 54.68 |
| 10 | −1.1508 | 0.5440 | 1.9340 | 18.90 |
| 11 | −3.1952 | 0.6165 | 1.0000 | |
| 12 | ∞ | 0.8160 | 1.5180 | 64.14 |
| 13 | ∞ | 0.0363 | 1.5120 | 64.05 |
| 14 | ∞ | 0.7253 | 1.6140 | 50.49 |
| 15 | ∞ | 0.0000 | 1.0000 | |
| IMG | ∞ | 0.0000 | | |

Example 4

Figure 8:
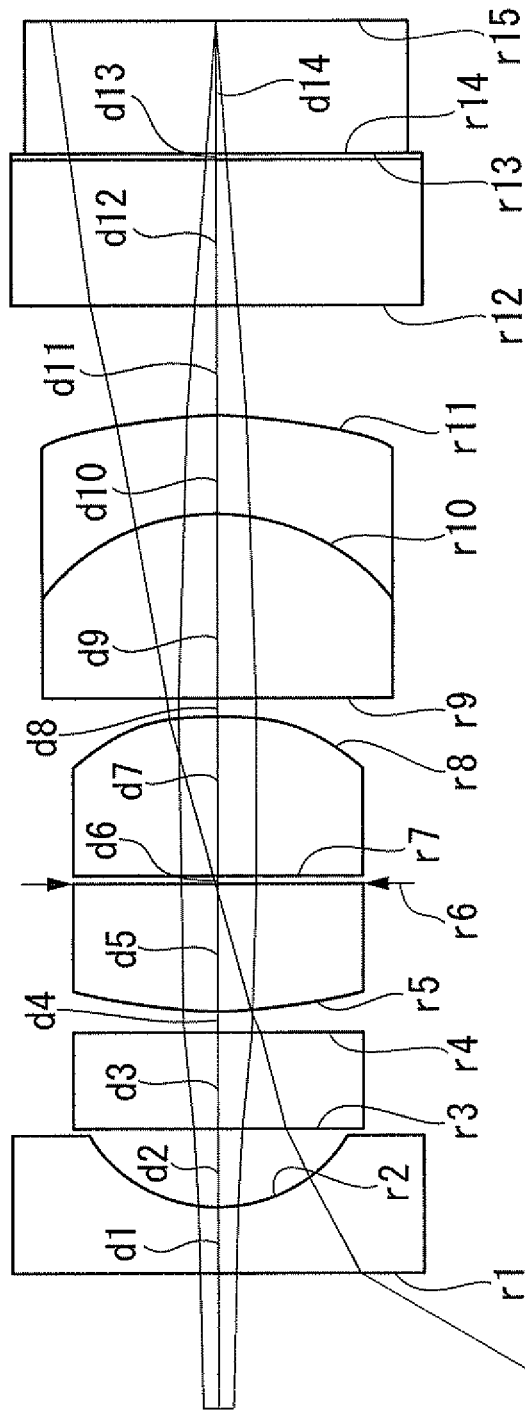
FIG. 8 is a lens cross-sectional diagram showing the configuration of an endoscope objective lens according to Example 4.
Figure 9:
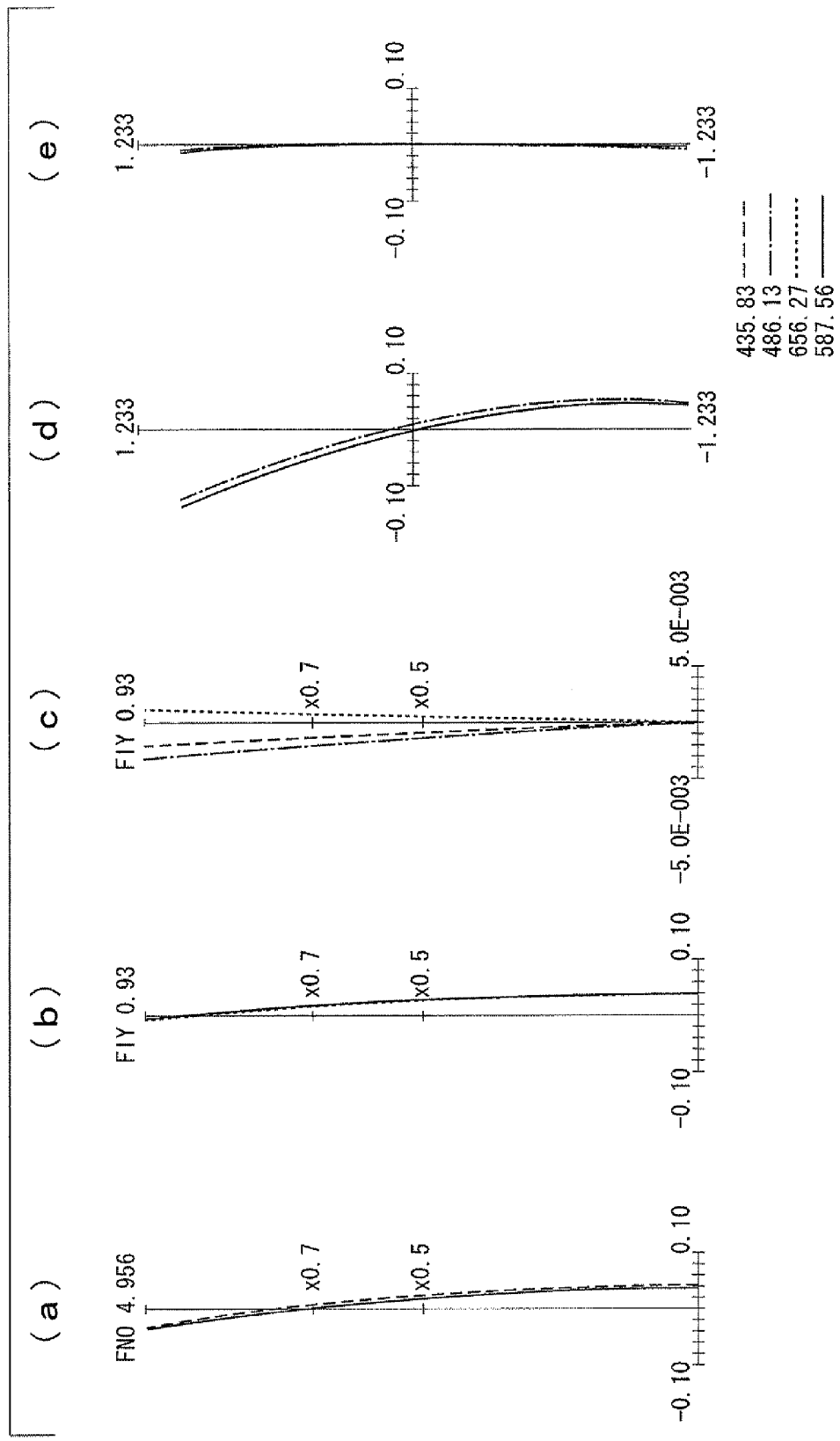
FIG. 9 includes various kinds of aberration diagrams of the endoscope objective lens in FIG. 8.

FIG. 8 shows the configuration of an endoscope objective lens according to Example 4, and the lens data thereof are shown below. FIG. 9 shows aberration diagrams of the endoscope objective lens according to this example.

The endoscope objective lens according to this example has the same configuration as the endoscope objective lens according to Example 1.

| Lens Data | | | | |
|---|---|---|---|---|
| Surface Number | r | d | nd | ν |
| OBJ | ∞ | 10.2043 | 1.0000 | |
| 1 | ∞ | 0.3580 | 1.7680 | 71.79 |
| 2 | 0.8504 | 0.4476 | 1.0000 | |
| 3 | ∞ | 0.5371 | 1.5180 | 75.00 |
| 4 | ∞ | 0.1074 | 1.0000 | |
| 5 | 3.0183 | 0.6982 | 1.7500 | 35.33 |
| 6(S) | ∞ | 0.0537 | 1.0000 | |
| 7 | ∞ | 0.8772 | 1.7290 | 54.68 |
| 8 | −1.3051 | 0.0895 | 1.0000 | |
| 9 | ∞ | 1.0204 | 1.7290 | 54.68 |
| 10 | −1.2585 | 0.5371 | 1.9230 | 18.90 |
| 11 | −3.1544 | 0.6087 | 1.0000 | |
| 12 | ∞ | 0.8056 | 1.5160 | 64.14 |
| 13 | ∞ | 0.0358 | 1.5100 | 64.05 |
| 14 | ∞ | 0.7161 | 1.6110 | 50.49 |
| 15 | ∞ | 0.0000 | 1.0000 | |
| IMG | ∞ | 0.0000 | | |

Example 5

Figure 10:
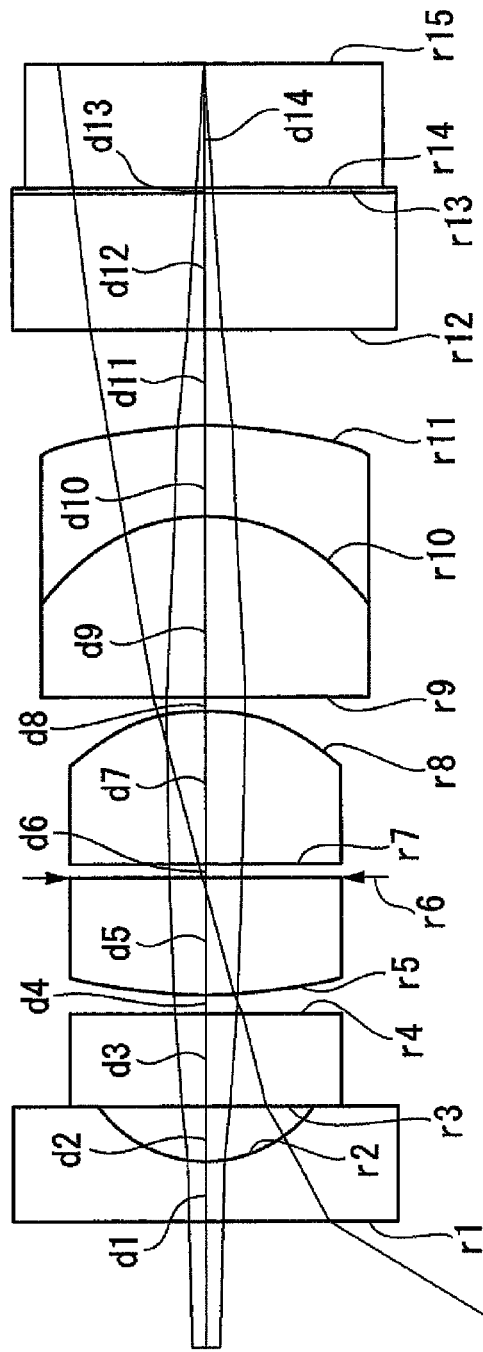
FIG. 10 is a lens cross-sectional diagram showing the configuration of an endoscope objective lens according to Example 5.
Figure 11:
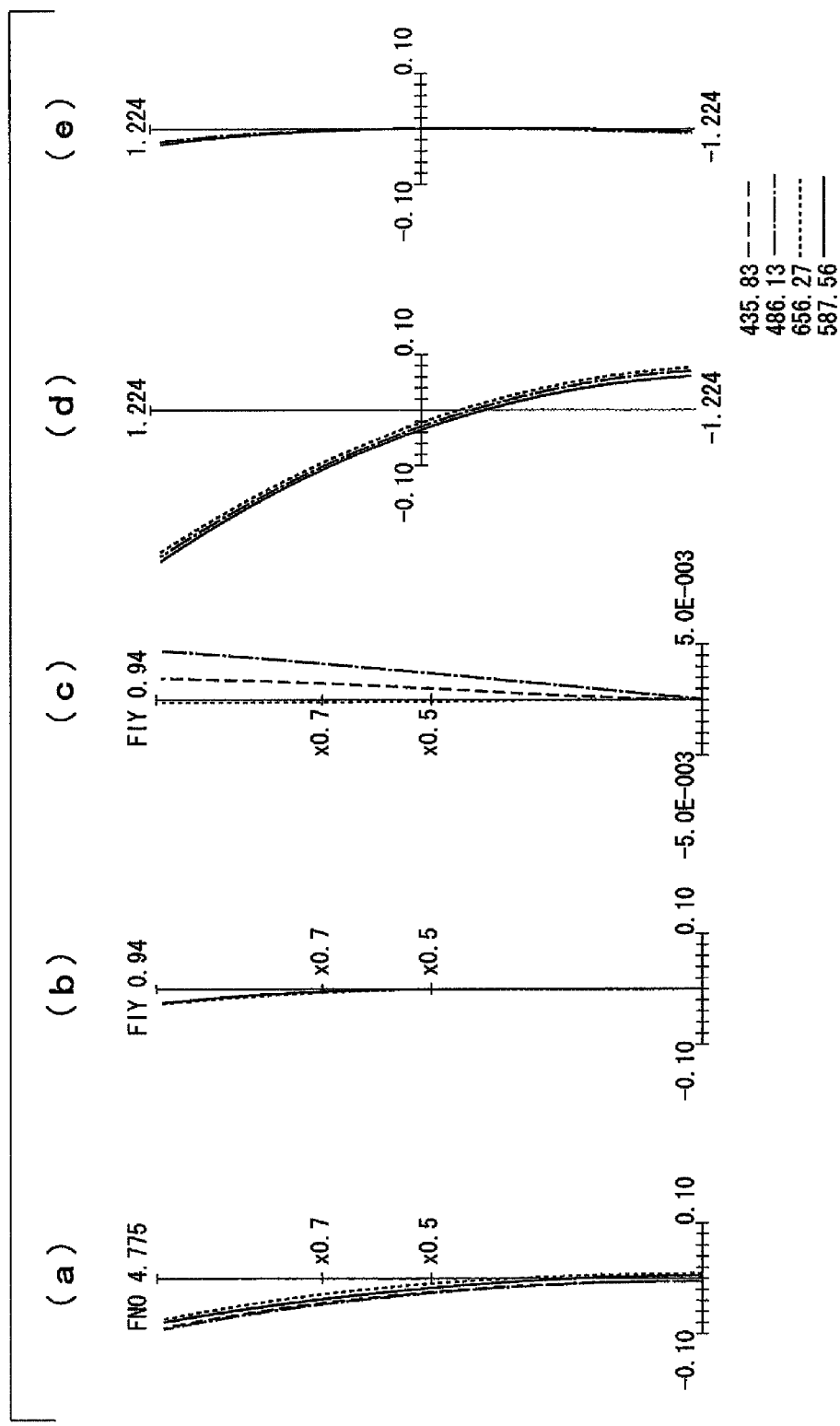
FIG. 11 includes various kinds of aberration diagrams of the endoscope objective lens in FIG. 10.

FIG. 10 shows the configuration of an endoscope objective lens according to Example 5, and the lens data thereof are shown below. FIG. 11 shows aberration diagrams of the endoscope objective lens according to this example.

The endoscope objective lens according to this example has the same configuration as the endoscope objective lens according to Example 1.

| Lens Data | | | | |
|---|---|---|---|---|
| Surface Number | r | d | nd | ν |
| OBJ | ∞ | 10.3379 | 1.0000 | |
| 1 | ∞ | 0.3627 | 1.7680 | 71.79 |
| 2 | 0.7993 | 0.3627 | 1.0000 | |
| 3 | ∞ | 0.5441 | 1.5180 | 75.00 |
| 4 | ∞ | 0.1088 | 1.0000 | |
| 5 | 3.5505 | 0.6936 | 1.9230 | 18.90 |
| 6(S) | ∞ | 0.0907 | 1.0000 | |
| 7 | ∞ | 0.9136 | 1.7000 | 65.00 |
| 8 | −1.2145 | 0.0907 | 1.0000 | |
| 9 | ∞ | 1.0772 | 1.7290 | 54.68 |
| 10 | −1.2237 | 0.5441 | 1.9230 | 18.90 |
| 11 | −3.1957 | 0.6166 | 1.0000 | |
| 12 | ∞ | 0.8162 | 1.5160 | 64.14 |
| 13 | ∞ | 0.0363 | 1.5100 | 64.05 |
| 14 | ∞ | 0.7255 | 1.6110 | 50.49 |
| 15 | ∞ | 0.0000 | 1.0000 | |
| IMG | ∞ | 0.0000 | | |

Example 6

Figure 12:
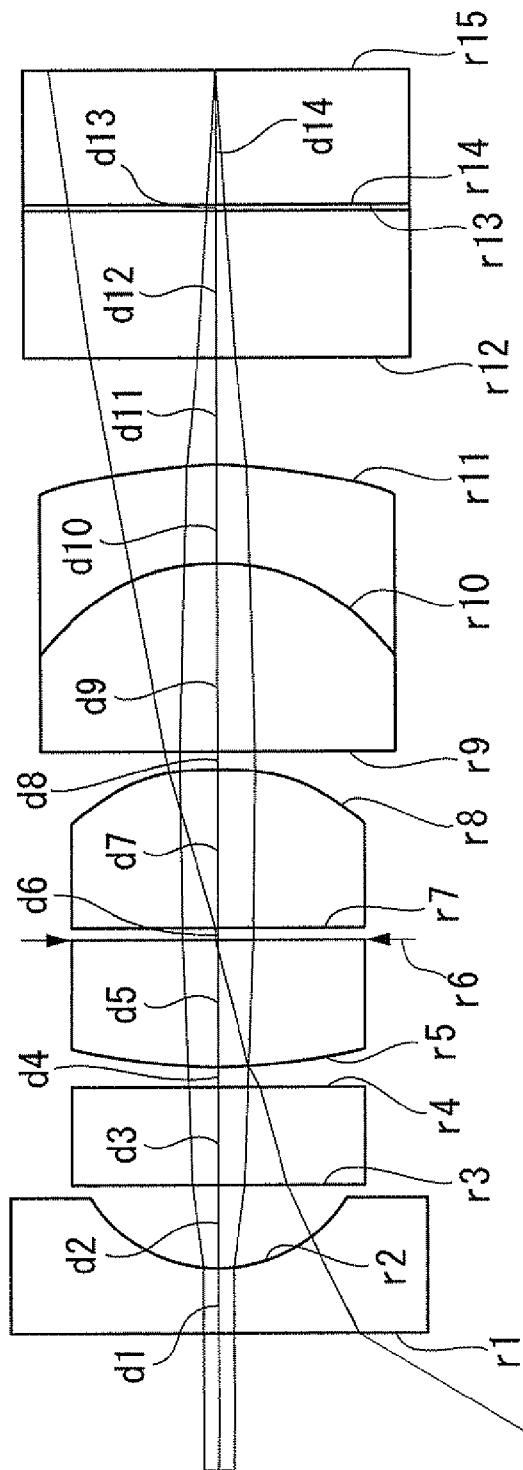
FIG. 12 is a lens cross-sectional diagram showing the configuration of an endoscope objective lens according to Example 6.
Figure 13:
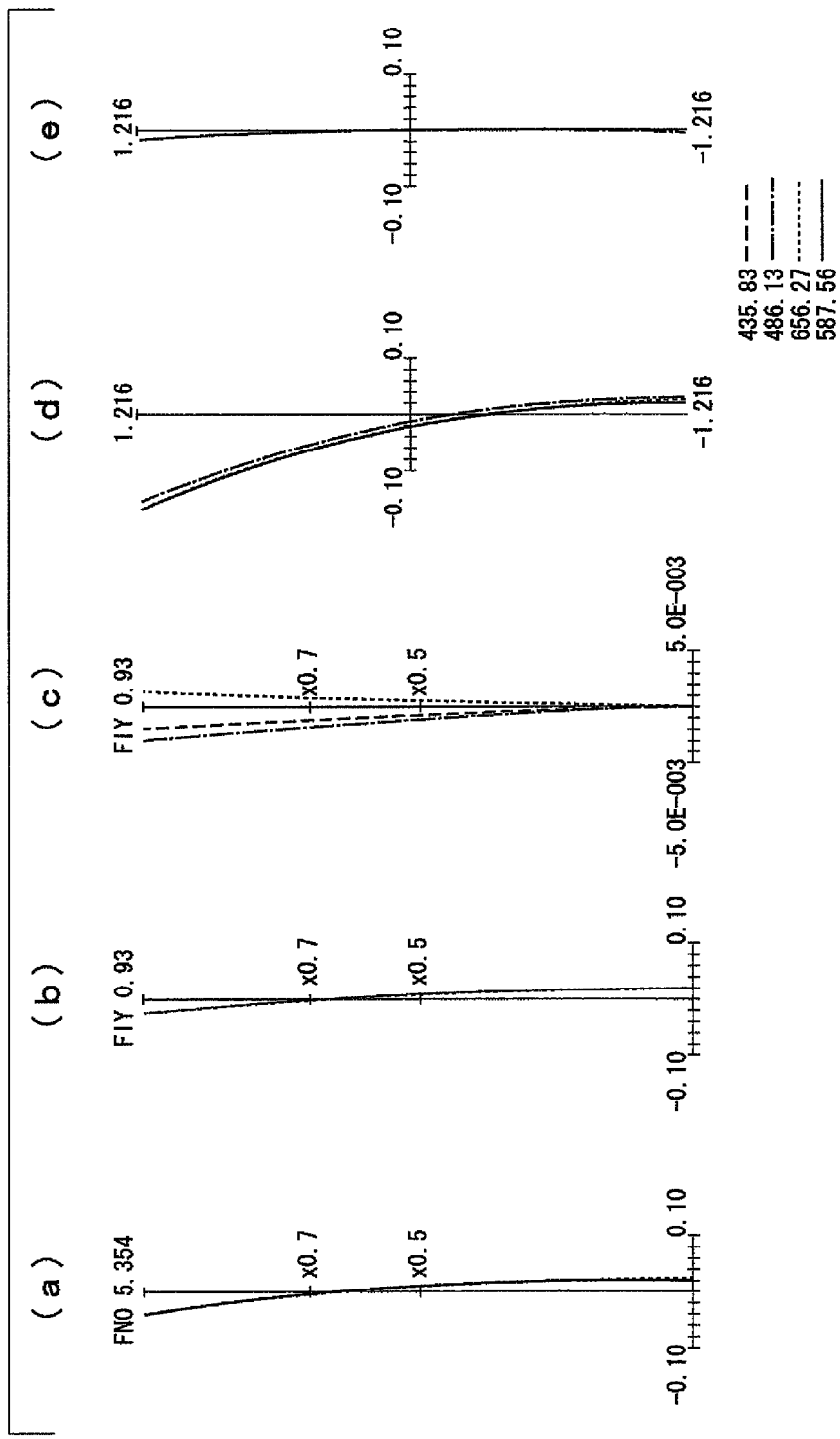
FIG. 13 includes various kinds of aberration diagrams of the endoscope objective lens in FIG. 12.

FIG. 12 shows the configuration of an endoscope objective lens according to Example 6, and the lens data thereof are shown below. Furthermore, FIG. 13 shows aberration diagrams of the endoscope objective lens according to this example.

The endoscope objective lens according to this example has the same configuration as the endoscope objective lens according to Example 1.

| Lens Data | | | | |
|---|---|---|---|---|
| Surface Number | r | d | nd | ν |
| OBJ | ∞ | 9.8584 | 1.0000 | |
| 1 | ∞ | 0.3585 | 1.7680 | 71.79 |
| 2 | 0.8514 | 0.4481 | 1.0000 | |
| 3 | ∞ | 0.5377 | 1.5180 | 74.70 |
| 4 | ∞ | 0.1075 | 1.0000 | |
| 5 | 3.022 | 0.6990 | 1.7500 | 35.33 |
| 6(S) | ∞ | 0.0538 | 1.0000 | |
| 7 | ∞ | 0.8783 | 1.7290 | 54.68 |
| 8 | −1.3067 | 0.0896 | 1.0000 | |
| 9 | ∞ | 1.0217 | 1.7290 | 54.68 |
| 10 | −1.2601 | 0.5377 | 1.9230 | 18.90 |
| 11 | −3.1583 | 0.6005 | 1.0000 | |
| 12 | ∞ | 0.8066 | 1.5160 | 64.14 |
| 13 | ∞ | 0.0358 | 1.5100 | 64.10 |
| 14 | ∞ | 0.7170 | 1.5060 | 50.20 |
| 15 | ∞ | 0.0000 | 1.0000 | |
| IMG | ∞ | 0.0000 | | |

Example 7

Figure 14:
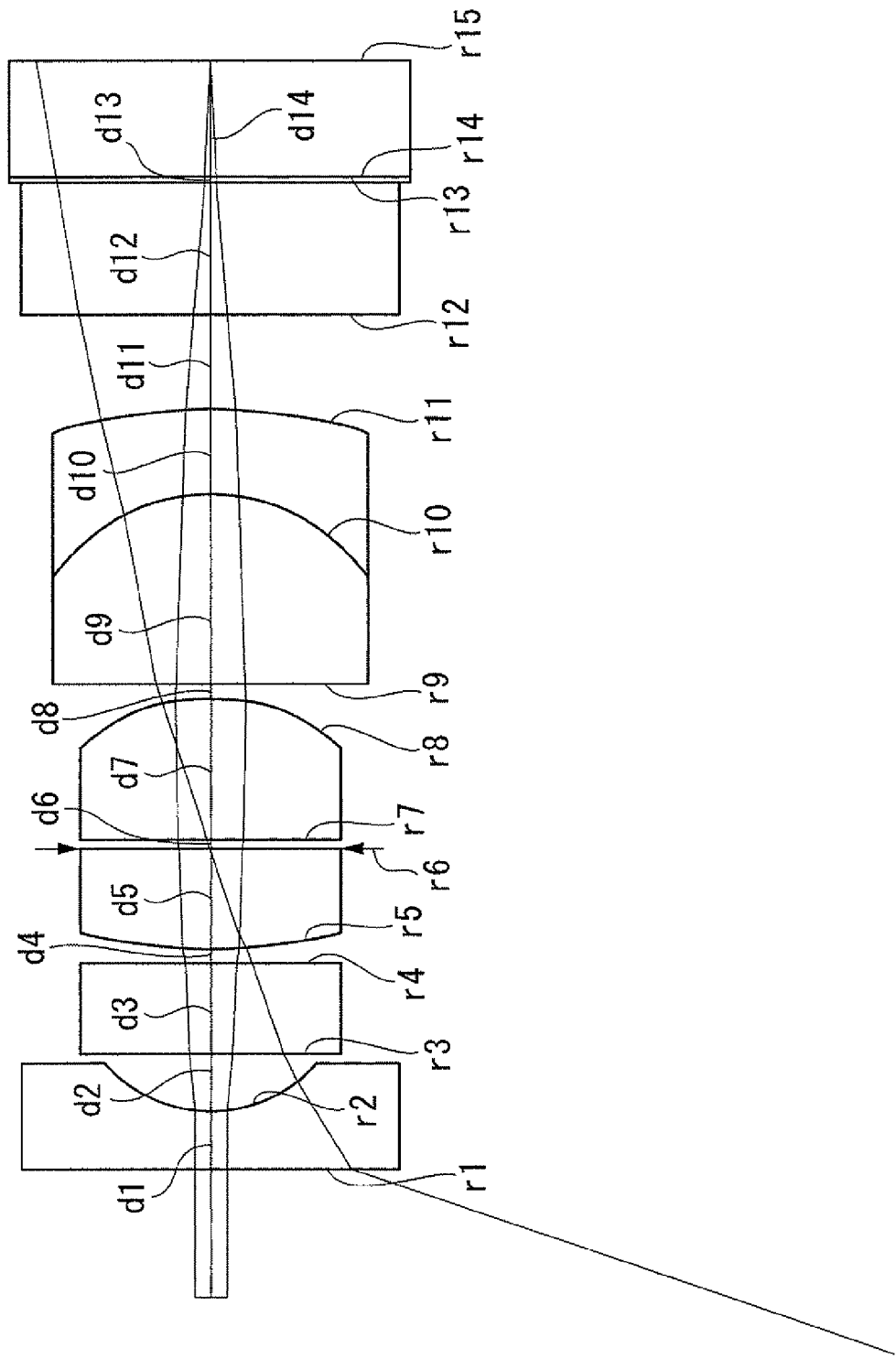
FIG. 14 is a lens cross-sectional diagram showing the configuration of an endoscope objective lens according to Example 7.
Figure 15:
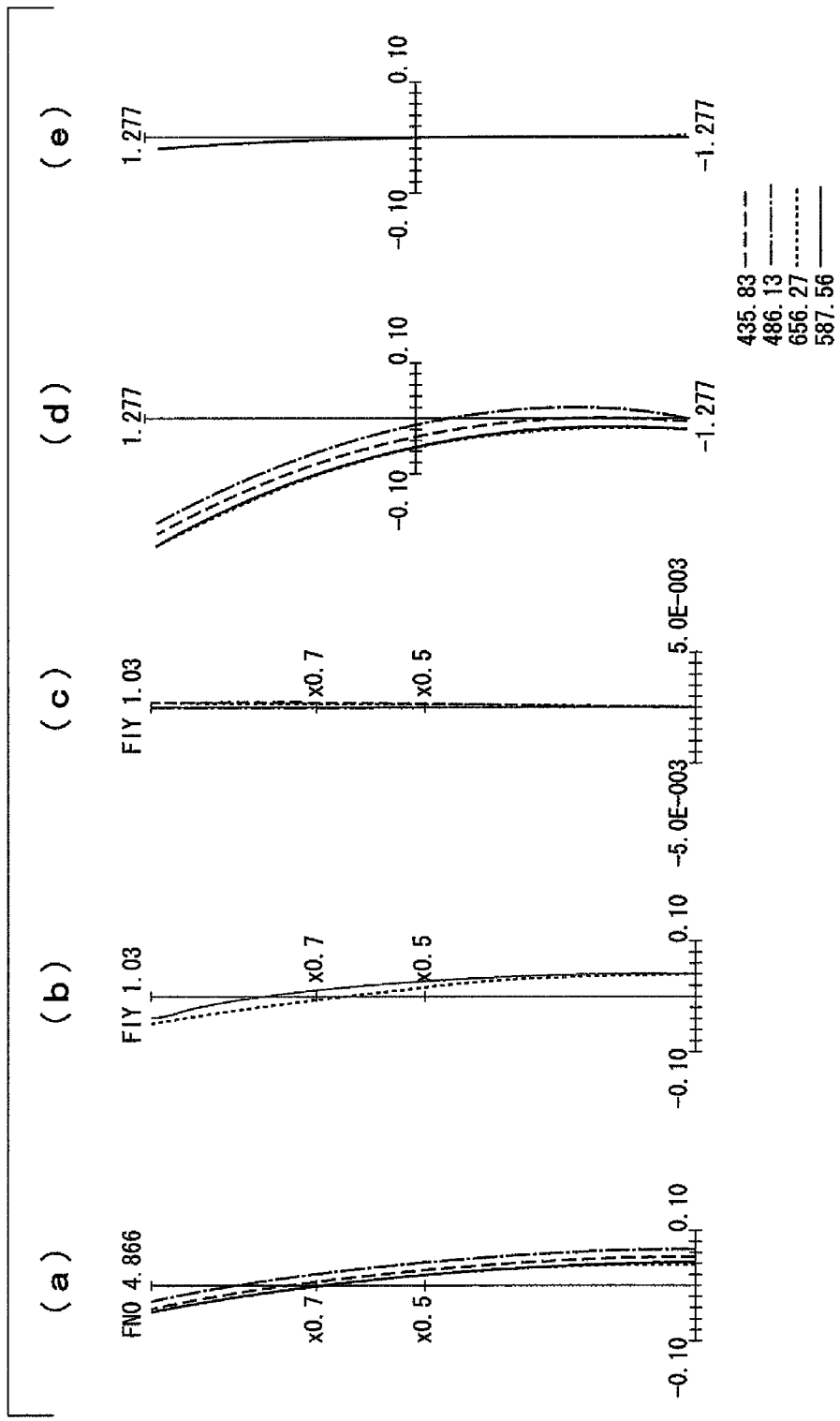
FIG. 15 includes various kinds of aberration diagrams of the endoscope objective lens in FIG. 14.

FIG. 14 shows the configuration of an endoscope objective lens according to Example 7, and the lens data thereof are shown below. Furthermore, FIG. 15 shows aberration diagrams of the endoscope objective lens according to this example.

The endoscope objective lens according to this example has the same configuration as the endoscope objective lens according to Example 1.

Example 8

Figure 16:
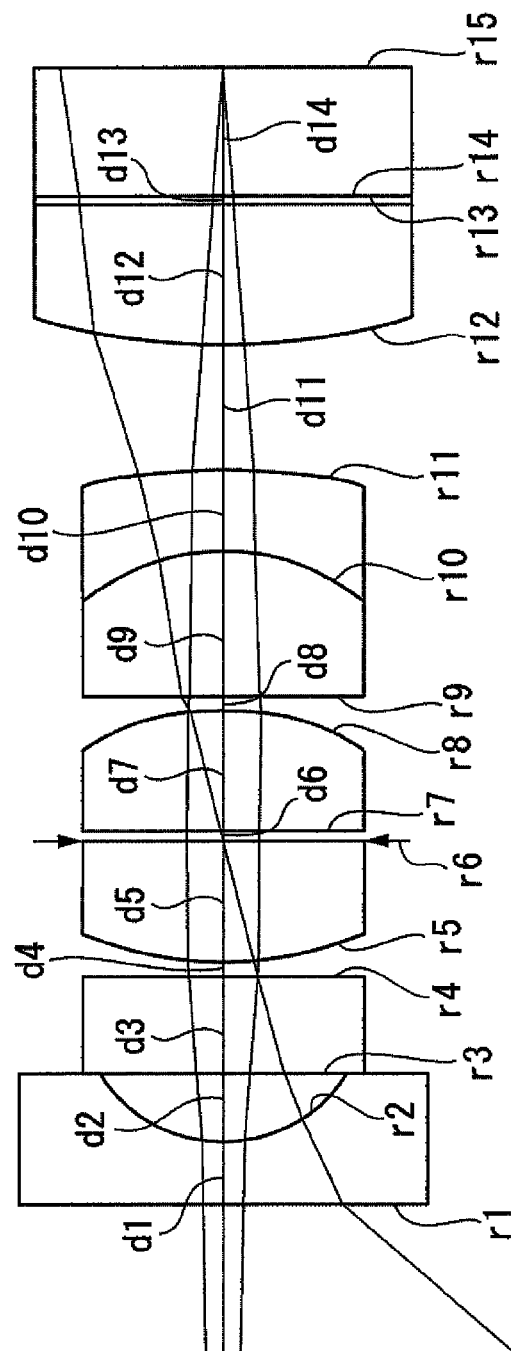
FIG. 16 is a lens cross-sectional diagram showing the configuration of an endoscope objective lens according to Example 8.
Figure 17:
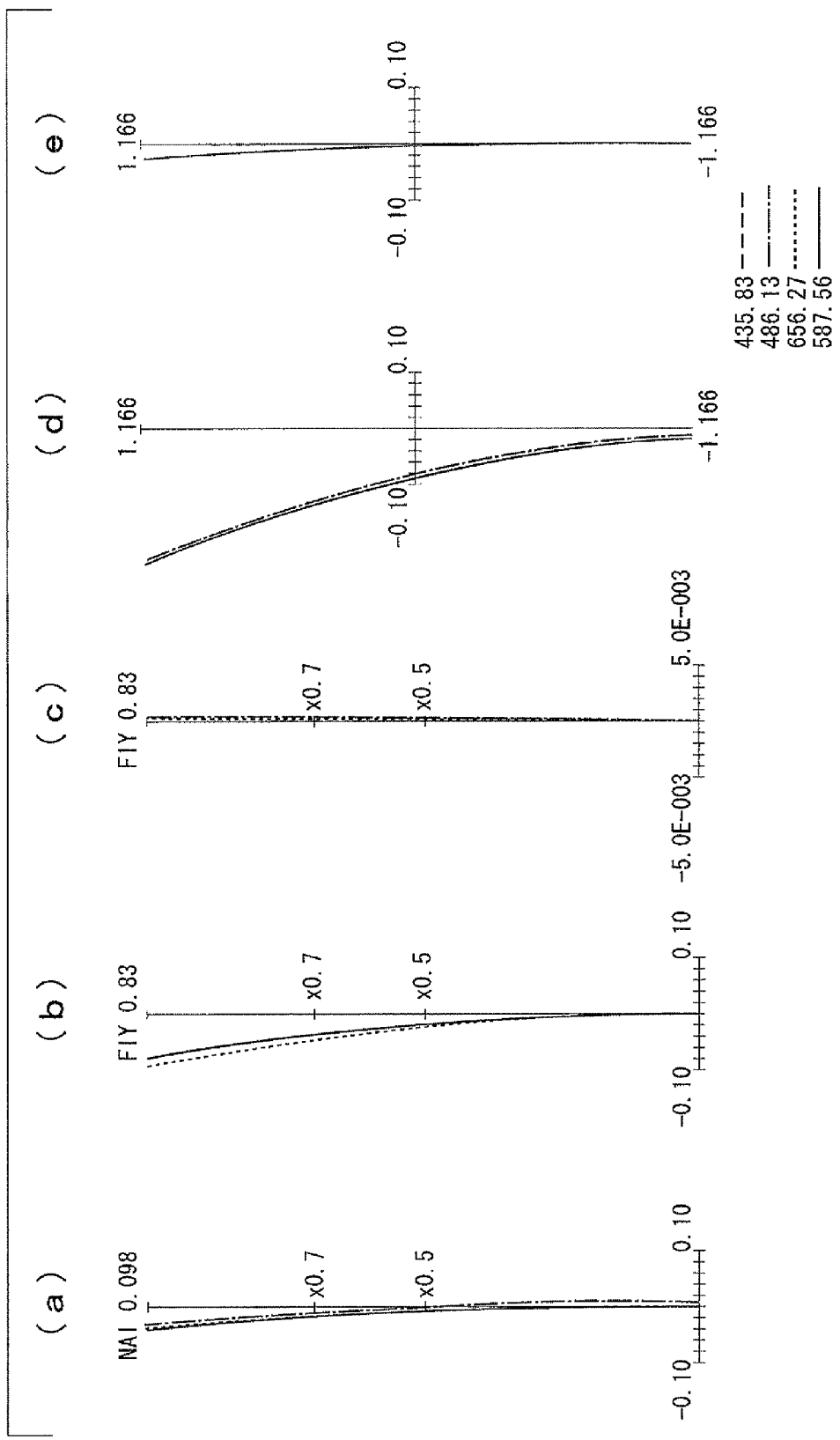
FIG. 17 includes various kinds of aberration diagrams of the endoscope objective lens in FIG. 16.

FIG. 16 shows the configuration of an endoscope objective lens according to Example 8, and the lens data thereof are shown below. Furthermore, FIG. 17 shows aberration diagrams of the endoscope objective lens according to this example.

The endoscope objective lens according to this example has a configuration different from that according to Example 1 in that it has a positive plano-convex lens, which serves as a sixth lens and whose convex surface faces the object side, behind the combined lens in the back group.

| Lens Data | | | | |
|---|---|---|---|---|
| Surface Number | r | d | nd | ν |
| OBJ | ∞ | 9.8401 | 1.0000 | 0.00 |
| 1 | ∞ | 0.3453 | 1.7680 | 71.79 |
| 2 | 0.8264 | 0.3453 | 1.0000 | |
| 3 | ∞ | 0.5179 | 1.5180 | 75.00 |
| 4 | ∞ | 0.1036 | 1.0000 | |
| 5 | 3.4154 | 0.5885 | 1.7500 | 35.33 |
| 6(S) | ∞ | 0.0518 | 1.0000 | |
| 7 | ∞ | 0.8294 | 1.7000 | 65.00 |
| 8 | −1.1205 | 0.0863 | 1.0000 | |
| 9 | ∞ | 1.1011 | 1.7290 | 54.68 |
| 10 | −1.1213 | 0.5179 | 1.9230 | 18.90 |
| 11 | −3.0418 | 0.5524 | 1.0000 | |
| 12 | ∞ | 0.7769 | 1.5160 | 64.14 |
| 13 | ∞ | 0.0345 | 1.5100 | 64.05 |
| 14 | ∞ | 0.6905 | 1.6110 | 50.49 |
| 15 | ∞ | 0.0000 | 1.0000 | |
| IMG | ∞ | 0.0000 | | |

Example 9

Figure 18:
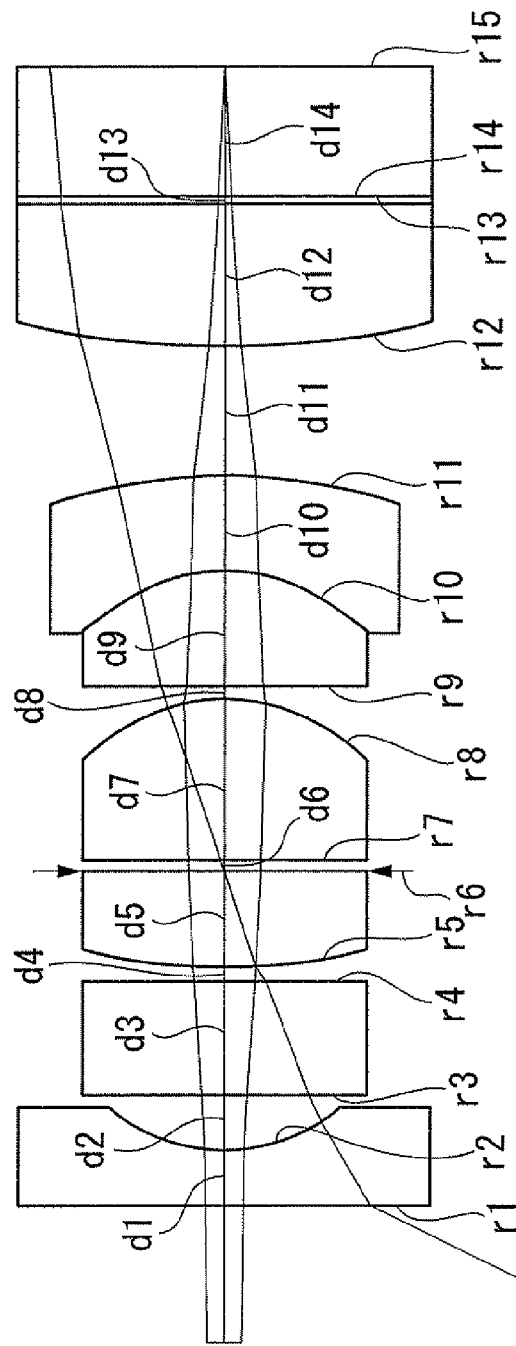
FIG. 18 is a lens cross-sectional diagram showing the configuration of an endoscope objective lens according to Example 9.
Figure 19:
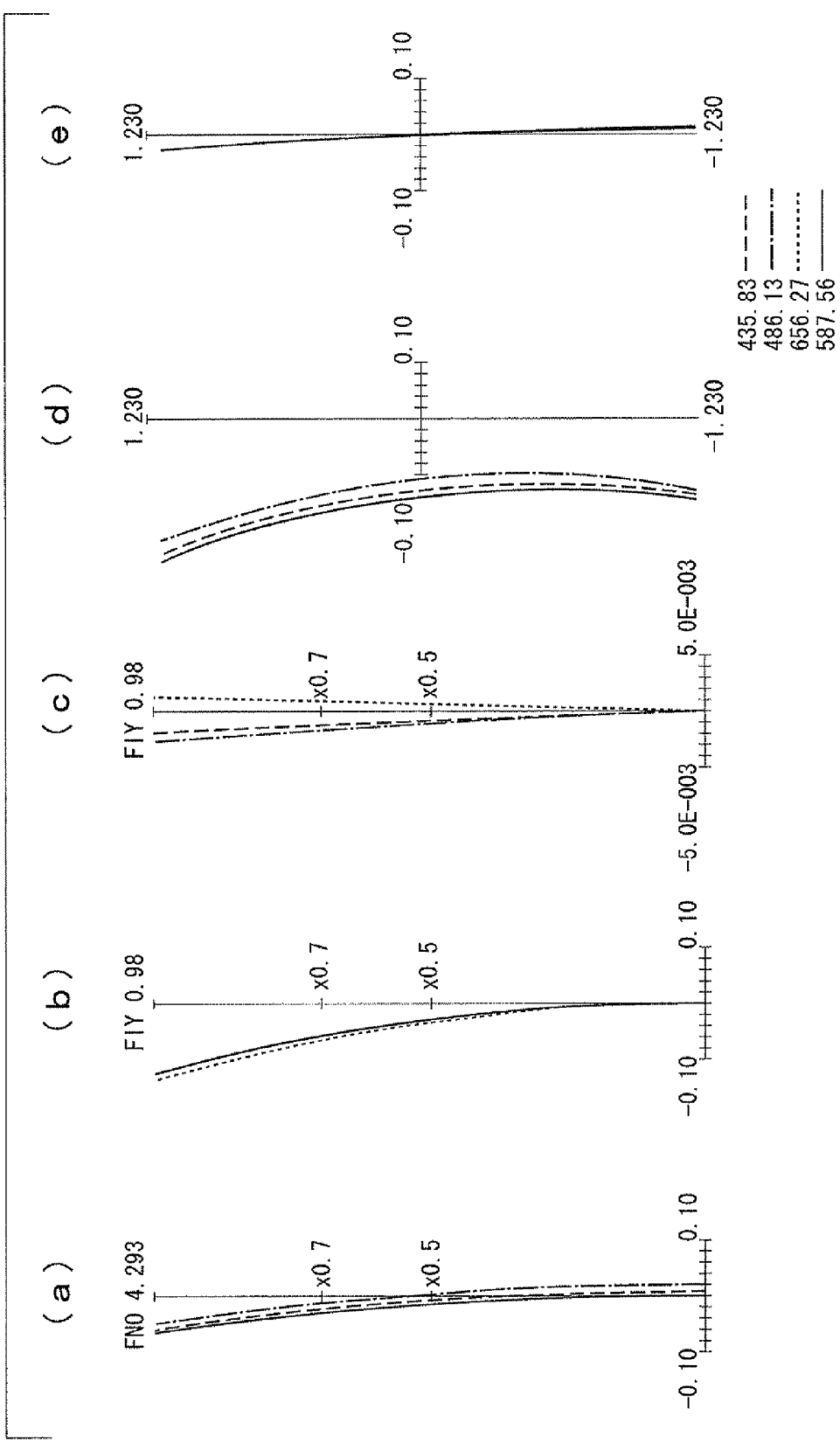
FIG. 19 includes various kinds of aberration diagrams of the endoscope objective lens in FIG. 18.

FIG. 18 shows the configuration of an endoscope objective lens according to Example 9, and the lens data thereof are shown below. Furthermore, FIG. 19 shows aberration diagrams of the endoscope objective lens according to this example.

The endoscope objective lens according to this example has the same configuration as Example 8.

| Lens Data | | | | |
|---|---|---|---|---|
| Surface Number | r | d | nd | ν |
| OBJ | ∞ | 9.1946 | 1.0000 | |
| 1 | ∞ | 0.3226 | 1.7710 | 71.70 |
| 2 | 0.7662 | 0.3549 | 1.0000 | |
| 3 | ∞ | 0.4839 | 1.5200 | 74.44 |
| 4 | ∞ | 0.0807 | 1.0000 | |
| 5 | 1.8244 | 0.6291 | 1.8830 | 40.76 |
| 6(S) | ∞ | 0.0484 | 1.0000 | |
| 7 | ∞ | 0.6130 | 1.7290 | 54.68 |
| 8 | −1.4631 | 0.0887 | 1.0000 | |
| 9 | ∞ | 0.7259 | 1.7290 | 54.68 |
| 10 | −1.0872 | 0.4033 | 1.9230 | 18.90 |
| 11 | −3.4262 | 0.6593 | 1.0000 | |
| 12 | 3.4956 | 0.7098 | 1.5160 | 64.14 |
| 13 | ∞ | 0.0323 | 1.5120 | 63.80 |
| 14 | ∞ | 0.6452 | 1.6140 | 50.20 |
| 15 | ∞ | 0.0000 | 1.0000 | |
| IMG | ∞ | 0.0000 | | |

Example 10

Figure 20:
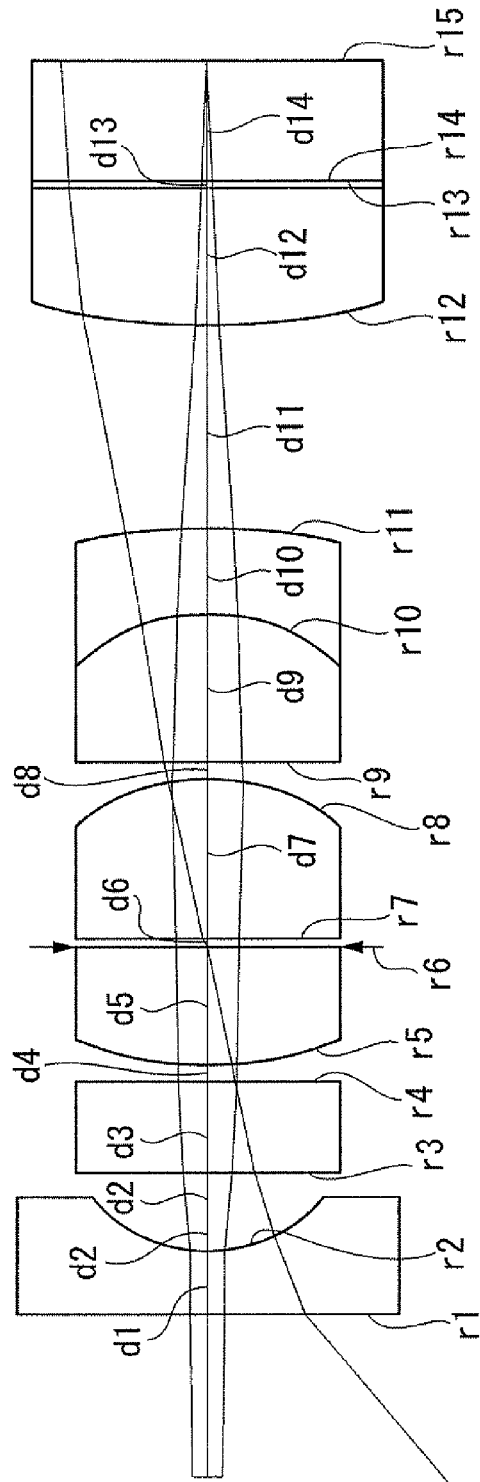
FIG. 20 is a lens cross-sectional diagram showing the configuration of an endoscope objective lens according to Example 10.
Figure 21:
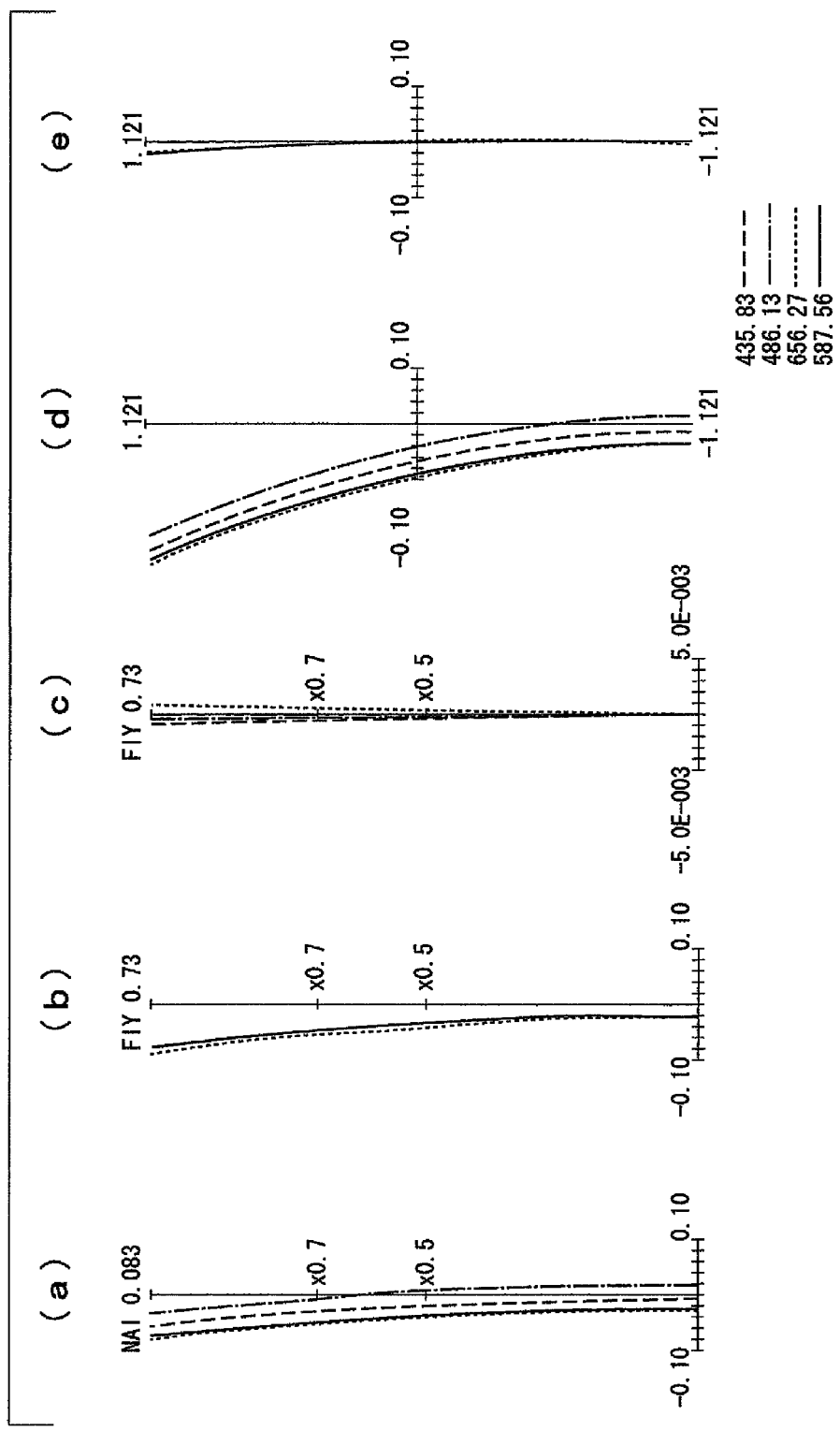
FIG. 21 includes various kinds of aberration diagrams of the endoscope objective lens in FIG. 20.

FIG. 20 shows the configuration of an endoscope objective lens according to Example 10, and the lens data thereof are shown below. Furthermore, FIG. 21 shows aberration diagrams of the endoscope objective lens according to this example.

The endoscope objective lens according to this example has the same configuration as Example 8.

| Lens Data | | | | |
|---|---|---|---|---|
| Surface Number | r | d | nd | ν |
| OBJ | ∞ | 10.0351 | 1.0000 | |
| 1 | ∞ | 0.3169 | 1.7680 | 71.79 |
| 2 | 1.0035 | 0.2887 | 1.0000 | |
| 3 | ∞ | 0.6162 | 1.5180 | 75.00 |
| 4 | ∞ | 0.0880 | 1.0000 | |
| 5 | 3.5911 | 0.5282 | 1.7500 | 35.33 |
| 6(S) | ∞ | 0.0528 | 1.0000 | |
| 7 | ∞ | 0.8726 | 1.6700 | 47.23 |
| 8 | −1.1315 | 0.0880 | 1.0000 | |
| 9 | ∞ | 0.6162 | 1.7290 | 54.68 |
| 10 | −1.1144 | 0.5282 | 1.9230 | 18.90 |
| 11 | −3.1021 | 0.7007 | 1.0000 | |
| 12 | 4.9101 | 0.7922 | 1.5160 | 64.14 |
| 13 | ∞ | 0.0352 | 1.5100 | 64.05 |
| 14 | ∞ | 0.7042 | 1.6110 | 50.49 |
| 15 | ∞ | 0.0000 | 1.0000 | |
| IMG | ∞ | 0.0000 | | |

Example 11

Figure 22:
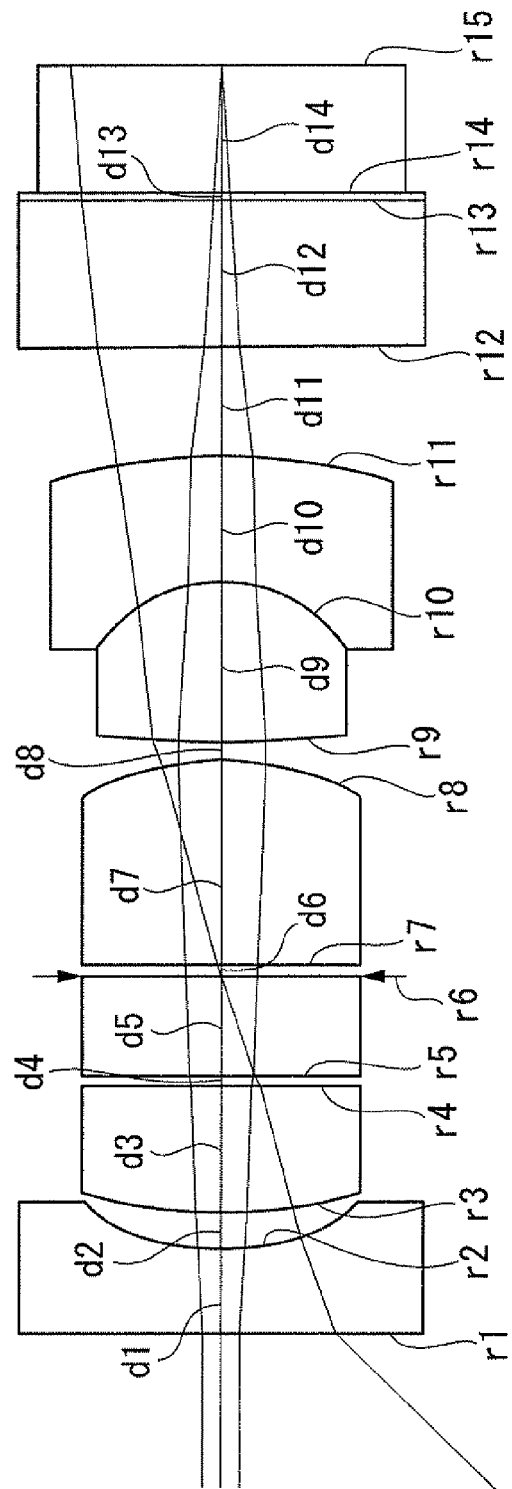
FIG. 22 is a lens cross-sectional diagram showing the configuration of an endoscope objective lens according to Example 11.
Figure 23:
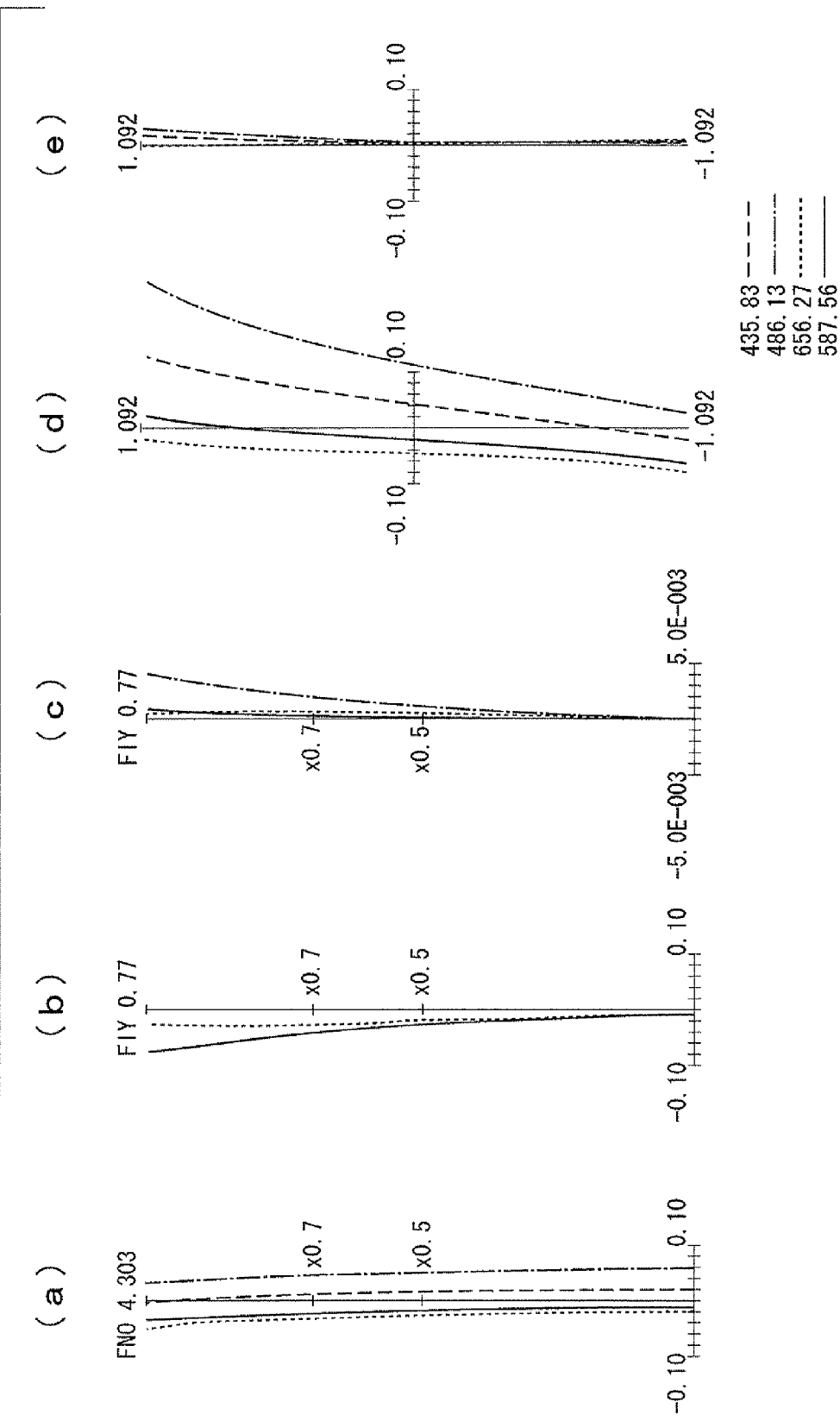
FIG. 23 includes various kinds of aberration diagrams of the endoscope objective lens in FIG. 22.

FIG. 22 shows the configuration of an endoscope objective lens according to Example 11, and the lens data thereof are shown below. Furthermore, FIG. 23 shows aberration diagrams of the endoscope objective lens according to this example.

The endoscope objective lens according to this example has a configuration different from that according to Example 1 in that a filter is disposed behind the second lens and in that a biconvex lens is used as the fourth lens.

| Lens Data | | | | |
|---|---|---|---|---|
| Surface Number | r | d | nd | ν |
| OBJ | ∞ | 8.1077 | 1.0000 | |
| 1 | ∞ | 0.3025 | 1.8830 | 40.76 |
| 2 | 0.7741 | 0.3581 | 1.0000 | |
| 3 | ∞ | 0.4267 | 1.5200 | 74.44 |
| 4 | ∞ | 0.0711 | 1.0000 | |
| 5 | 1.7943 | 0.5547 | 1.8830 | 40.76 |
| 6(S) | ∞ | 0.0427 | 1.0000 | |
| 7 | ∞ | 0.7390 | 1.5890 | 61.14 |
| 8 | −1.1321 | 0.0782 | 1.0000 | |
| 9 | ∞ | 0.6869 | 1.7290 | 54.68 |
| 10 | −0.9587 | 0.4004 | 1.9230 | 18.90 |
| 11 | −3.0212 | 0.9550 | 1.0000 | |
| 12 | 5.1223 | 0.6259 | 1.5160 | 64.14 |
| 13 | ∞ | 0.0284 | 1.5120 | 63.80 |
| 14 | ∞ | 0.5690 | 1.6140 | 50.20 |
| 15 | ∞ | 0.0000 | 1.0000 | |
| IMG | ∞ | 0.0000 | | |

Lens Data

| Surface Number | r | d | nd | ν |
|---|---|---|---|---|
| OBJ | ∞ | 8.9419 | 1.0000 | |
| 1 | ∞ | 0.3922 | 2.1820 | 33.01 |
| 2 | 1.1808 | 0.1771 | 1.0000 | |
| 3 | 2.1954 | 0.6258 | 1.8880 | 40.76 |
| 4 | ∞ | 0.0471 | 1.0000 | |
| 5 | ∞ | 0.4960 | 1.5200 | 75.00 |
| 6(S) | ∞ | 0.0471 | 1.0000 | |
| 7 | ∞ | 1.0040 | 1.7470 | 49.34 |
| 8 | −1.3674 | 0.0784 | 1.0000 | |
| 9 | 6.213 | 0.7844 | 1.8880 | 40.76 |
| 10 | −0.7703 | 0.6040 | 1.9340 | 18.90 |
| 11 | −3.7046 | 0.5370 | 1.0000 | |
| 12 | ∞ | 0.7059 | 1.5180 | 64.14 |
| 13 | ∞ | 0.0314 | 1.5120 | 64.05 |
| 14 | ∞ | 0.6275 | 1.6140 | 50.49 |
| 15 | ∞ | 0.0000 | 1.0000 | |
| IMG | ∞ | 0.0000 | | |

Example 12

Figure 24:
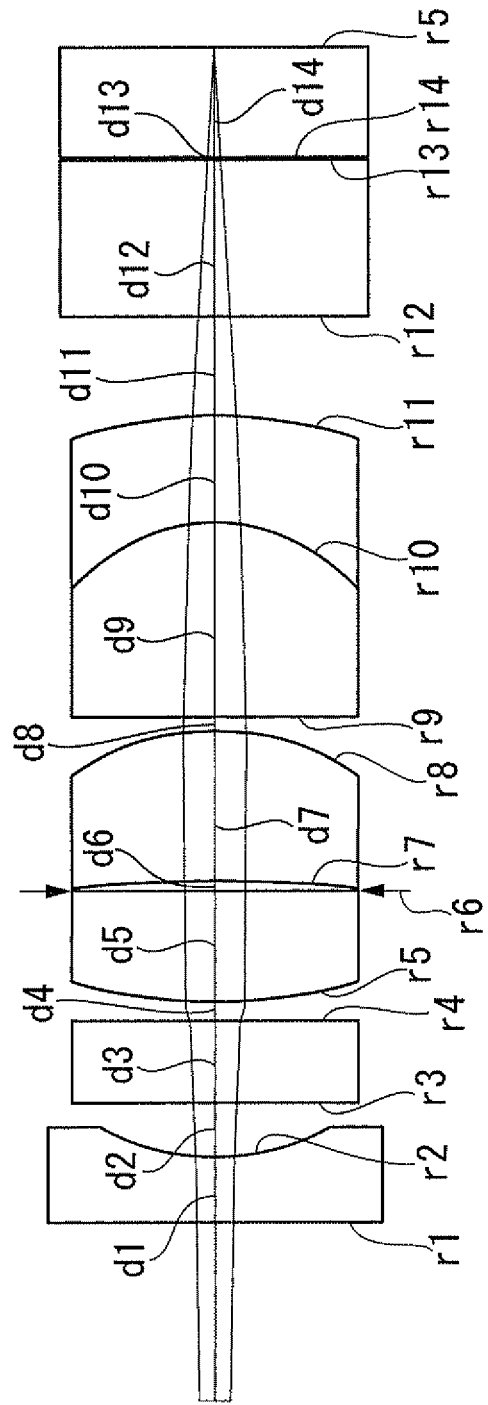
FIG. 24 is a lens cross-sectional diagram showing the configuration of an endoscope objective lens according to Example 12.
Figure 25:
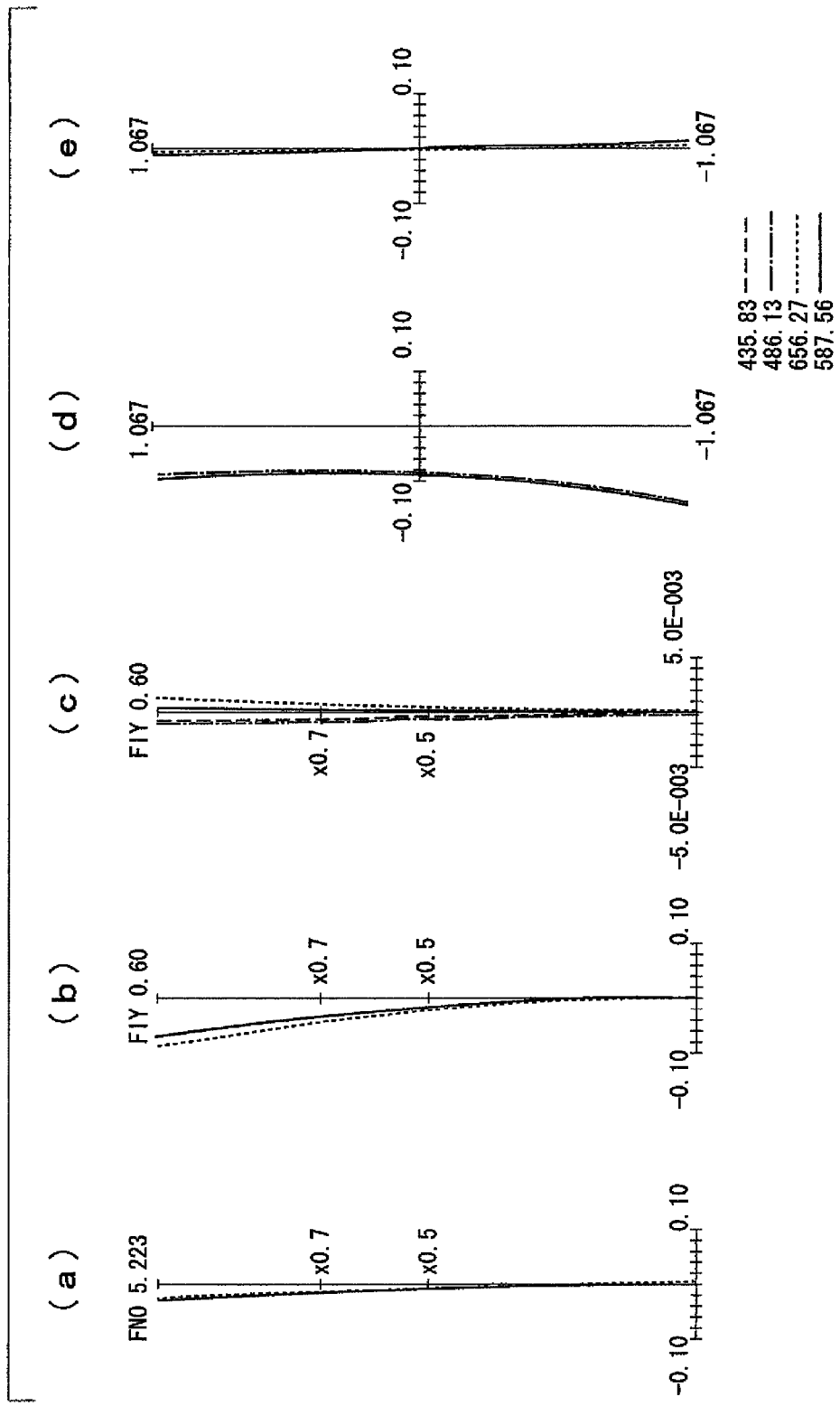
FIG. 25 includes various kinds of aberration diagrams of the endoscope objective lens in FIG. 24.

FIG. 24 shows the configuration of an endoscope objective lens according to Example 12, and the lens data thereof are shown below. Furthermore, FIG. 25 shows aberration diagrams of the endoscope objective lens according to this example.

The endoscope objective lens according to this example has a configuration different from that according to Example 1 in that a positive meniscus lens is used as the third lens.

Lens Data

| Surface Number | r | d | nd | ν |
|---|---|---|---|---|
| OBJ | ∞ | 6.6534 | 1.0000 | |
| 1 | ∞ | 0.2918 | 1.7680 | 71.79 |
| 2 | 1.1883 | 0.2335 | 1.0000 | |
| 3 | ∞ | 0.3502 | 1.5180 | 75.00 |
| 4 | ∞ | 0.0700 | 1.0000 | |
| 5 | 2.2526 | 0.4727 | 1.7500 | 35.33 |
| 6(S) | ∞ | 0.0350 | 1.0000 | |
| 7 | −4.4676 | 0.6494 | 1.9300 | 45.00 |
| 8 | −1.1325 | 0.0584 | 1.0000 | |
| 9 | ∞ | 0.8238 | 1.7290 | 54.68 |
| 10 | −0.871 | 0.4669 | 1.9230 | 18.90 |
| 11 | −2.0567 | 0.4253 | 1.0000 | |
| 12 | ∞ | 0.6420 | 1.5160 | 64.14 |
| 13 | ∞ | 0.0233 | 1.5100 | 64.05 |
| 14 | ∞ | 0.4669 | 1.6110 | 50.49 |
| 15 | ∞ | 0.0000 | 1.0000 | |
| IMG | ∞ | 0.0000 | | |

Example 13

Figure 26:
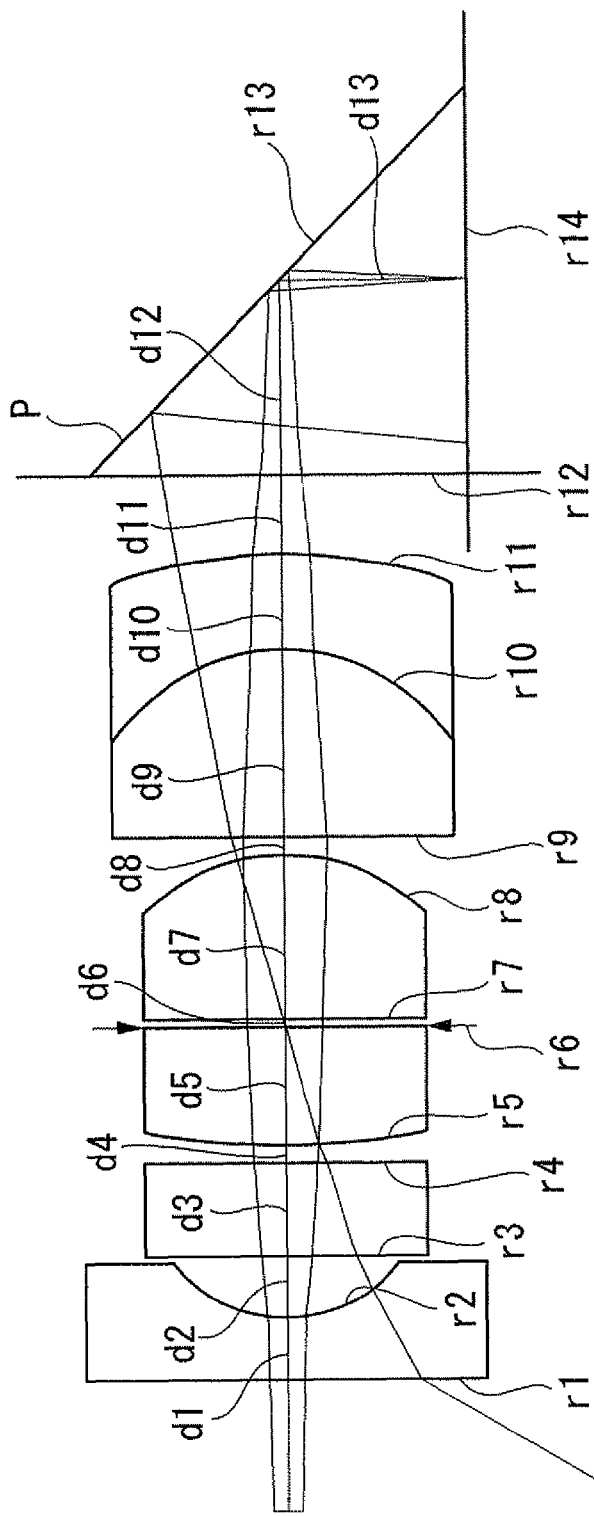
FIG. 26 is a lens cross-sectional diagram showing the configuration of an endoscope objective lens according to Example 13.

FIG. 26 shows the configuration of an endoscope objective lens according to Example 13, and the lens data thereof are shown below. The endoscope objective lens according to this example has the same configuration as the endoscope objective lens according to Example 1 from the first lens to the combined lens, and an optical-path changing device P, which changes light in a perpendicular direction, is disposed on the object side of the image acquisition device.

Lens Data

| Surface Number | r | d | nd | ν |
|---|---|---|---|---|
| OBJ | ∞ | 10.3427 | 1.0000 | |
| 1 | ∞ | 0.3629 | 1.7680 | 71.79 |
| 2 | 0.8535 | 0.3386 | 1.0000 | |
| 3 | ∞ | 0.5444 | 1.5180 | 75.00 |
| 4 | ∞ | 0.1089 | 1.0000 | |
| 5 | 3.8738 | 0.6858 | 1.7500 | 35.33 |
| 6(S) | ∞ | 0.0544 | 1.0000 | |
| 7 | ∞ | 0.9389 | 1.7000 | 65.00 |
| 8 | −1.1501 | 0.0907 | 1.0000 | |
| 9 | ∞ | 1.0901 | 1.7290 | 54.68 |
| 10 | −1.2076 | 0.5444 | 1.9230 | 18.90 |
| 11 | −3.1972 | 0.4595 | 1.0000 | |
| 12 | ∞ | 1.1000 | 1.8830 | 40.76 |
| 13 (Reflection Plane) | ∞ | 1.1000 | 1.8830 | 40.76 |
| 14 | ∞ | 0.0000 | 1.0000 | |
| IMG | ∞ | 0.0000 | | |

Table 1 shows the respective parameters in Examples 1 to 13 and the values in Conditional Expression (1) to (3).

TABLE 1

| Example | Focal Length of Entire | Conditional Expression (1) | | | Conditional Expression (2) | | | Conditional Expression (3) | | |
|---|---|---|---|---|---|---|---|---|---|---|
| | | n3 | ν3 | −ν3/12 + 5.5 | df | Ih | df/Ih | f3 | r3 | \|f3/r3\| |
| 1 | 1.000 | 1.7 | 65 | 0.0833 | 1.6777 | 0.9399 | 1.7849 | 1.643 | −1.1501 | 1.4286 |
| 2 | 1.000 | 1.68 | 62 | 0.3333 | 1.6819 | 0.94 | 1.7893 | 1.6389 | −1.1187 | 1.465 |
| 3 | 1.000 | 1.74 | 48 | 1.5 | 1.6755 | 0.9393 | 1.7837 | 1.6036 | −1.1926 | 1.3447 |
| 4 | 1.000 | 1.73 | 54.68 | 0.9433 | 1.7902 | 0.9273 | 1.9305 | 1.7898 | −1.3051 | 1.3714 |
| 5 | 1.000 | 1.7 | 65 | 0.0833 | 1.7092 | 0.9395 | 1.8193 | 1.735 | −1.2145 | 1.4286 |
| 6 | 1.000 | 1.73 | 54.68 | 0.9433 | 1.7924 | 0.9285 | 1.9305 | 1.7843 | −1.3067 | 1.3655 |
| 7 | 1.000 | 1.7 | 65 | 0.0833 | 1.5553 | 1.0341 | 1.504 | 1.6007 | −1.1205 | 1.4286 |
| 8 | 1.000 | 1.73 | 54.68 | 0.9433 | 1.5486 | 0.8275 | 1.8713 | 2.0065 | −1.4631 | 1.3714 |
| 9 | 1.000 | 1.67 | 47.23 | 1.5642 | 1.5211 | 0.9771 | 1.5568 | 1.6888 | −1.1315 | 1.4925 |
| 10 | 1.000 | 1.59 | 61.14 | 0.405 | 1.4107 | 0.7297 | 1.9333 | 1.9217 | −1.1321 | 1.6974 |
| 11 | 1.000 | 1.74 | 49.34 | 1.3883 | 1.346 | 0.7675 | 1.7536 | 1.8311 | −1.3674 | 1.3391 |
| 12 | 1.000 | 1.93 | 45 | 1.75 | 1.1264 | 0.6046 | 1.8629 | 1.4832 | −1.1325 | 1.3096 |
| 13 | 1.000 | 1.7 | 65 | 0.0833 | 1.6777 | 0.9399 | 1.7849 | 1.643 | −1.1501 | 1.4286 |

(Additional Items)

An invention having the following configurations is derived from the above-described examples.

(Additional Item 1)

1. An endoscope objective lens comprising, in sequence from an object side:
   a front group;
   an aperture stop; and
   a back group, wherein
   the front group includes, in sequence from the object side, a negative first lens whose concave surface faces an image side and a positive second lens whose convex surface faces the object side and whose flat surface or concave surface is located on the image side, and a filter disposed between the first lens and the second lens, and
   the back group includes, in sequence from the object side, a positive third lens whose convex surface faces the image side, and a combined lens formed of a plano-convex lens or a biconvex lens and a negative meniscus lens, and
   the endoscope objective lens satisfies the following Conditional Expression (1) and (2)

$$n3 > -v3/12 + 5.5 \quad (1)$$

$$2.0 > df/Ih > 1.5 \quad (2)$$

where n3 is the refractive index of the third lens, and v3 is the Abbe number of the third lens, df is the sum of the thickness of an optical element and the inter-surface distance from the apex of the concave surface of the first lens to the aperture stop, and Ih is the maximum image height.

(Additional Item 2)

The endoscope objective lens according to Additional Item 1, wherein the following Conditional Expression (3) is satisfied $$|f3/r3| > 1.3 \quad (3)$$

where f3 is the focal length of the third lens and r3 is the image-plane-side radius of curvature of the third lens.

(Additional Item 3)

The endoscope objective lens according to Additional Items 1 or 2, wherein the back group includes a plurality of positive lenses.

(Additional Item 4)

The endoscope objective lens according to any one of Additional Items 1 to 3, wherein the filter is an optical filter, which is not limited to an infrared-cut filter or a color-correcting filter.

(Additional Item 5)

The endoscope objective lens according to any one of Additional Items 1 to 4, wherein the first lens is made of a material having chemical resistance or sterilization resistance.

(Additional Item 6)

The endoscope objective lens according to any one of Additional Items 1 to 5, comprising an optical-path changing device, such as a prism or the like.

(Additional Item 7)

An endoscope comprising the endoscope objective lens according to any one of Additional Items 1 to 6.

What is claimed is:

1. An endoscope objective lens comprising, in sequence from an object side:
   a front group;
   an aperture stop; and
   a back group, wherein
   the front group includes, in sequence from the object side, a negative first lens whose concave surface faces an image side and a positive second lens whose convex surface faces the object side and whose flat surface or concave surface is located on the image side, and a filter disposed between the first lens and the second lens, and
   the back group includes, in sequence from the object side, a positive third lens whose convex surface faces the image side, and a combined lens formed of a plano-convex lens or a biconvex lens and a negative meniscus lens, and
   the endoscope objective lens satisfies the following Conditional Expressions (1) and (2)

$$n3 > -v3/12 + 5.5 \quad (1)$$

$$2.0 > df/Ih > 1.5 \quad (2)$$

where n3 is the refractive index of the third lens, and v3 is the Abbe number of the third lens, df is the sum of the thickness of an optical element and the inter-surface distance from the apex of the concave surface of the first lens to the aperture stop, and Ih is the maximum image height.

2. The endoscope objective lens according to claim 1, wherein the following Conditional Expression (3) is satisfied $$|f3/r3| > 1.3 \quad (3)$$

where f3 is the focal length of the third lens, and r3 is the image-plane-side radius of curvature of the third lens.

3. An endoscope comprising the endoscope objective lens according to claim 1.

* * * * *